(12) United States Patent
Heroux et al.

(10) Patent No.: US 6,635,418 B2
(45) Date of Patent: *Oct. 21, 2003

(54) ASSAY METHODS FOR NUCLEIC ACID IN A SAMPLE

(75) Inventors: Jeffrey A. Heroux, Middletown, MD (US); Marta L. Corcoran, Rockville, MD (US); Savitha M. Rao, Gaithersburg, MD (US)

(73) Assignee: Igen International, Inc., Gaithersburg, MD (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/023,483

(22) Filed: Feb. 13, 1998

(65) Prior Publication Data

US 2001/0014446 A1 Aug. 16, 2001

(51) Int. Cl.[7] ............................ C12Q 1/68; C12P 19/34; C07H 21/00; C07H 21/04
(52) U.S. Cl. ................. 435/6; 435/91.2; 435/91.52; 435/91.51; 536/25.32; 536/25.6
(58) Field of Search ...................... 435/91.2, 91.52, 435/91.51, 403; 536/25.32, 26.6

(56) References Cited

U.S. PATENT DOCUMENTS 5,043,272 A  *  8/1991  Hartley ..................... 435/91
5,364,759 A  *  11/1994  Caskey et al. .............. 435/6
5,413,906 A  *  5/1995  Eberle et al. ............... 435/5
5,599,662 A  *  2/1997  Respess ...................... 435/5
6,096,499 A  *  8/2000  Kozlowski et al. .......... 435/6

OTHER PUBLICATIONS

Wu et al. The ligation amplification reaction (LAR)—amplification of specific DNA sequences using sequential rounds of template–dependent ligation. Genomics, vol. 4, p. 560–569.*

Merrick et al. Threshold, a complete system for quantitative analysis of total DNA, protein impurities and relevant proteins, 1992, Biotech Forum Europe, vol. 9(6), pp. 398–403.*

Feinberg, Andrew P., et al, *Analytical Biochemistry*, 132, 6–13 (1983), "A Technique for Radiolabeling DNA Restriction Endonuclease Fragments to High Specific Activity".

Briggs, Jonathan, et al, *Anal. Chem.*, 1991, 63, 850–859, "Quantitation of DNA and Protein Impurities in Biopharmaceuticals".

* cited by examiner

*Primary Examiner*—Jeffrey Siew
*Assistant Examiner*—Joyce Tung
(74) *Attorney, Agent, or Firm*—Nixon & Vanderhye P.C.

(57) ABSTRACT

The present invention relates to a method for the determination of the presence and amount of DNA in a sample. The method is based on the use of a nucleic acid template dependent enzyme in combination with a random primer to generate an enzymatic product which incorporates a binding species and a detectable species covalently linked.

62 Claims, No Drawings

ASSAY METHODS FOR NUCLEIC ACID IN A SAMPLE

FIELD OF INVENTION

The present invention relates to a method for the determination of the presence and amount of DNA in a sample. The method is based on the use of a nucleic acid template dependent enzyme in combination with a random primer to generate an enzymatic product which incorporates a binding species and a detectable species covalently linked.

BACKGROUND OF INVENTION

The development of therapeutic biopharmaceuticals for human injection generated through recombinant deoxyribonucleic acid (DNA) technology has resulted in new standards for product purity. Viral contamination of several vaccines initially demonstrated the safety risk associated with the products generated from recombinant technology. Thus, contamination of products by host cell DNA could be a biological hazard for the recipient. The primary concern of regulatory agencies is the potential contamination of product with oncogenes or infectious viral DNA. DNA in high amounts (1–10 $\mu$g) has been shown to cause tumors in mice. Because the risk associated with exposure of 100 pg of DNA per dose is negligible, the WHO (World Health Organization) currently requires the DNA in all biopharmaceuticals to be below 100 pg per dose. Thus, methodologies that accurately determine picogram amounts of DNA have become a requisite in the biopharmaceutical field. Several different methodologies exist for quantitation of DNA. Each method has limitations with respect to dynamic range for accurate DNA quantitation and biases due to base composition. Because of the multitude of manipulations during the purification process of a typical protein therapeutic sample, the DNA in the final protein therapeutic is most likely sheared (less than 1,000 basepairs) and exists in both single and/or double stranded forms.

1. Current Methods for Determination of DNA

The most widely accepted method for quantitation of DNA is absorbance spectroscopy. At 260 nm, each base has a specific absorption spectra. Using a spectrophotometer, an average absorbance is obtained which directly reflects the base composition of the DNA. This reading is based on the base composition of the DNA because at an OD of 260, the extinction coefficient of adenosine and guanosine bases is more than cytosine or thymine. The discrimination on base composition and the low level of sensitivity (1 ug DNA) are several limitations of this method. Another significant drawback of this method is the interference caused by impurities such as organic compounds and protein.

A second method for quantitation of DNA utilizes fluorescence spectroscopy.

Upon binding DNA, the fluorescence characteristics of flourochromes change such that energy emitted at a particular wavelength is proportional to the amount of DNA in the sample. Typically, unknowns are extrapolated from a standard curve of known calibrated DNA standards. Several dyes currently exist that have the capacity to bind single or double stranded DNA, as well as mRNA. Ethidium bromide is one dye that binds to DNA without base discrimination and can be used to accurately quantitate at least 100 ng of DNA. Although the Hoechst dye (33258, Molecular Probes Eugene, Oreg.) quantitates 10 ng of DNA accurately (DyNA Quant; Hoefer Pharmacia Biotech), it preferentially binds AT rich regions of DNA. The Beacon DNA dye (PanVera Corp., Madison, Wis.) detects 25 ng/ml of double stranded DNA only. Molecular Probes manufactures two dyes that the company claims to accurately detect 25 pg/ml of double stranded DNA (PicoGreen) and 100 pg/ml of single stranded DNA (OliGreen). If both forms of DNA are represented in a given sample, two separate determinations must be performed. A PCR based method exists that amplifies the DNA and measures the relative amounts of DNA by changes in fluorescence polarization. All these fluorochromes have limitations with respect to the ability to detect low picogram amounts of DNA.

Another method for quantitation of DNA utilizes a specific labeled probe to quantitate a unique sequence of host DNA. Currently, the Southern slot-blot method is accepted by the FDA for the final determination of total DNA in protein therapeutic samples. Specifically, a labeled probe generated from purified host DNA is used to quantitate the presence of specific sequences of DNA in the final protein therapeutic sample. Although slot-blot detects low picogram quantities of DNA, the results represent only the host DNA. Therefore, contaminating DNA from other genes of the host or from other contaminants (such as bacterial DNA) are not detected. Major disadvantages of slot-blot include a relatively narrow dynamic range, a technically challenging protocol, a time consuming, and difficult protocol to troubleshoot. Additionally, the semi-quantitative results obtained from this method are directly dependent on the specific activity of the probe which can be highly variable.

Another commonly used methodology (for quantitation of 2–200 picograms of DNA) is an assay that captures DNA by binding to a single stranded DNA binding protein and detects the DNA via a enzymatic amplification of signal from a enzyme labeled anti-DNA antibody. Disadvantages to the total DNA assay performed on a threshold system (Molecular Devices) include the narrow dynamic range, the technically challenging and time consuming protocol. In addition the inability to accurately detect fragments of DNA below 872 basepairs severely limits the overall sensitivity of the assay. In fact, decreasing the size of DNA below 872 basepairs inhibits the detection of fragments greater than 872 basepairs. The lack of sensitivity for smaller DNA fragments is a major disadvantage of this methodology because the significant quantity of DNA in protein therapeutic samples is fragmented.

Chemical modification of DNA bases followed by detection via an enzyme labeled antibody that recognizes specific modified base is another technique that claims to detect pg amounts of DNA in samples. However, this method is complicated, extremely technically challenging, requires handing and requires subsequent disposal of hazardous waste, and extensive data manipulation.

2. Current Technology Using Random Oligonucleotide Priming

DNA dependent DNA polymerases incorporate deoxyribonucleotide to the 3' hydroxyl terminus of a double stranded primed DNA molecule. The synthesis of the new strand of DNA occurs in a 5' to 3' direction with respect to the synthesized strand. Each nucleotide that is incorporated during the polymerization is complementary to the one opposite to it in the template(dA pairs with dT, dC with dG). The reaction requires four deoxyribonucleotide triphosphates (dNTPs) and magnesium ions. Many of the polymerases have a 3'–5' exonuclease inherently associated with the polymerase activity. During DNA synthesis, the exonuclease activity performs a proofreading function by removing mismatched and modified nucleotides. One property of DNA polymerases that becomes important for the random priming reactions is the ability to continuously incorporate nucleotides without dissociating from the primer template (processivity). The low processivity associated with the klenow fragment (C-terminus) of DNA polymerase allows incorporation of less than 10 nucleotides into the primer template and thus maximizes the generation of signal. An outline of the properties of some polynucleotide dependent polymerases are provided in the table below.

| Enzyme | 3'-5' exonuclease | Polymerase rate | Processivity |
| --- | --- | --- | --- |
| klenow fragment | low | intermediate | low |
| Reverse transcriptase | none | slow | intermediate |
| Taq DNA polymerase | none | fast | high |

Several kits have been generated based on the properties of these polymerases. These protocols have become widely acceptable methodologies for labeling DNA and generating probes. Included in these methods are nick-translation of double stranded DNA and random priming of DNA using hexamer oligonucleotides. Both these protocols utilize DNA polymerases to incorporate the signal moiety (labeled-dNTP) into the DNA. In addition to DNA polymerase, terminal transferase can also be used to generate a labeled DNA. The detection of DNA using these protocols is dependent upon hybridization of a labeled DNA probe to a complementary strand of DNA/RNA. Many commercially available kits use these acceptable methodologies for labeling DNA. One kit format utilizes a "biotinylated hexamer mix" in conjunction with a biotinylated dNTP mix to generate a biotinylated DNA probe using a random priming methodology. This probe is hybridized to target DNA and the signal generated via an enzyme mediated chemiluminescence that is sensitive to low picogram amounts of DNA. Another kit utilizes a random nanomer, instead of a hexamer, and incorporates a fluorescein-dNTP into the DNA. An alternative format to random priming utilizes incorporation of digoxigenin-dUTP into the DNA which is detected by labeled anti-digoxigenin antibody. See also U.S. Pat. No. 5,043,272 which describes the use of random sequences for amplification.

In addition, a method of polymerase activity by incubating the polymerase with a template nucleic acid, one detectable mononucleoside triphosphate and one immobilizable nucleoside triphosphate, binding the immobilizable nucleotides to a solid phase and detecting the bound detectable nucleotides and tests based thereon U.S. Pat. No. 5,413,906 has been described.

OBJECTS OF THE INVENTION

It is an object of this invention to provide methods and kits for determining the presence and amount of nucleic acid in a sample using random primers and nucleic acid template dependent enzymes.

SUMMARY OF THE INVENTION

This invention includes a method for the detection and/or quantitation of nucleic acid in a sample, which comprises; mixing at least one random primer (advantageously one or two primers) at least 4 nucleotides in length (advantageously 6–10 in length), having at least one detectable species (advantageously 1–3 detectable species) with a sample nucleic acid, adding at least one NTP (advantageously 1–3 NTPs) having at least one binding species (advantageously 1–3 binding species) and optionally at least one NTP (advantageously 3–5 NTPs), adding at least one nucleic acid polymerase (advantageously 1–3 polymerases), incubating this mixture under conditions which allow the at least one nucleic acid polymerase to be active, contacting this mixture with at least one solid phase (advantageously 1–3 solid phases) and detecting and/or quantitating the amount of nucleic acid in the sample by detecting and/or quantitating the amount of the at least one detectable species bound to said solid phase.

This invention also includes a method for the detection and/or quantitation of nucleic acid in a sample, which comprises; mixing at least one random primer (advantageously one or two primers) at least 4 nucleotides in length (advantageously 6–10 in length), having at least one binding species (advantageously 1–3 binding species) with a sample nucleic acid, adding at least one NTP (advantageously 1–3 NTPs) having at least one detectable species (advantageously 1–3 detectable species) and optionally at least one NTP (advantageously 3–5 NTPs), adding at least one nucleic acid polymerase (advantageously 1–3 polymerases), incubating this mixture under conditions which allow the at least one nucleic acid polymerase to be active, contacting this mixture with at least one solid phase (advantageously 1–3 solid phases) and detecting and/or quantitating the amount of nucleic acid in the sample by detecting and/or quantitating the amount of the at least one detectable species bound to said solid phase.

This invention also includes a method for the detection and/or quantitation of nucleic acid in a sample, which comprises; mixing at least one random primer (advantageously one or two primers) at least 4 nucleotides in length (advantageously 6–10 in length), with a sample nucleic acid, adding at least one NTP (advantageously 1–3 NTPs) having at least one binding species (advantageously 1–3 binding species) and optionally at least one NTP (advantageously 1–3 NTPs), having at least one detectable species (advantageously 1–3 detectable species) and optionally at least one NTP (advantageously 3–5 NTPs), adding at least one nucleic acid polymerase (advantageously 1–3 polymerases), incubating this mixture under conditions which allow the at least one nucleic acid polymerase to be active, contacting this mixture with at least one solid phase (advantageously 1–3 solid phases), detecting and/or quantitating the amount of nucleic acid in the sample by detecting and/or quantitating the amount of the at least one detectable species or the amount of the at least one binding species bound to said solid phase.

This invention also includes a method for the detection and/or quantitation of nucleic acid in a sample, which comprises: mixing at least one labeled random primer (advantageously one or two primers) at least 4 nucleotides in length (advantageously 6–10 in length), having at least one binding species (advantageously 1–3 binding species) and optionally at least one detectable species (advantageously 1–3 detectable species), with a sample nucleic acid, adding at least one nucleic acid ligase (advantageously 1–3 ligase), adding at least one NTP (advantageously 1–3 NTPs), incubating this mixture under conditions which allow said at least one nucleic acid ligase to be active, contacting this mixture with at least one solid phase (advantageously 1–3 solid phases), and detecting and/or quantitating the amount of nucleic acid in the sample by detecting and/or quantitating the amount of the at least one detectable species or the amount of the at least one binding species bound to the solid phase.

This invention also includes a method for the detection and/or quantitation of nucleic acid in a sample, which comprises; mixing at least one labeled random primer (advantageously one or two primers) at least 4 nucleotides in length (advantageously 6–10 in length), having at least one binding species (advantageously 1–3 binding species) and optionally at least one detectable species (advantageously 1–3 detectable species), with a sample nucleic acid, adding at least one nucleic acid ligase (advantageously 1–3 ligase), and at least one nucleic acid polymerase (advantageously 1–3 polymerase), adding at least one NTP (advantageously 3–5 NTPs), incubating this mixture under conditions which allow the at least one nucleic acid ligase and at least one nucleic acid polymerase to be active, contacting this mixture with at least one solid phase (advantageously 1–3 solid phases), and detecting and/or quantitating the amount of nucleic acid in the sample by detecting and/or quantitating the amount of the at least one detectable species or the amount of the at least one binding species bound to the solid phase.

This invention also includes a method for the detection and/or quantitation of nucleic acid in a sample, which comprises: mixing at least one random primer (advantageously one or two primers) at least 4 nucleotides in length (advantageously 6–10 in length), having at least one detectable species (advantageously 1–3 detectable species), with a sample nucleic acid, adding at least one NTP (advantageously 1–3 NTPs), having at least one binding species (advantageously 1–3 binding species) and optionally at least one NTP (advantageously 3–5 NTPs), adding at least one nucleic acid polymerase (advantageously 1–3 polymerase), incubating this mixture under conditions which allow said at least one nucleic acid polymerase to be active and quantitating the amount of nucleic acid in the sample by detecting and/or quantitating the amount of the at least one detectable species or the amount of the at least one binding species.

This invention also includes a method for the detection and/or quantitation of nucleic acid in a sample, which comprises; mixing at least one random primer (advantageously one or two primers) at least 4 nucleotides in length (advantageously 6–10 in length), having at least one binding species (advantageously 1–3 binding species), with a sample nucleic acid, adding at least one NTP (advantageously 1–3 NTPs), having at least one detectable species (advantageously 1–3 detectable species), and optionally at least one NTP (advantageously 3–5 NTPs), adding at least one nucleic acid polymerase (advantageously 1–3 polymerase), incubating this mixture under conditions which allow said at least one nucleic acid polymerase to be active and quantitating the amount of nucleic acid in the sample by detecting and/or quantitating the amount of the at least one detectable species or the amount of the at least one binding species.

This invention also includes a method for the detection and/or quantitation of nucleic acid in a sample, which comprises; mixing at least one random primer (advantageously one or two primers) at least 4 nucleotides in length (advantageously 6–10 in length), with a sample nucleic acid, adding at least one NTP (advantageously 1–3 NTPs) having at least one binding species (advantageously 1–3 binding species), and optionally at least one NTP (advantageously 1–3 NTPs) having at least one label (advantageously 1–3 labels), and optionally at least one NTP (advantageously 3–5 NTPs), adding at least one nucleic acid polymerase (advantageously 1–3 polymerase), incubating this mixture under conditions which allow the at least one nucleic acid polymerase to be active and quantitating the amount of nucleic acid in the sample by detecting and/or quantitating the amount of said at least one label or the amount of the at least one binding species.

This invention also includes a method for the detection and/or quantitation of nucleic acid in a sample, which comprises: mixing at least one labeled random primer (advantageously one or two primers) at least 4 nucleotides in length (advantageously 6–10 in length), having at least one binding species (advantageously 1–3 binding species), and optionally at least one detectable species (advantageously 1–3 detectable species), with a sample nucleic acid, adding at least one nucleic acid ligase (advantageously 1–3 ligase), adding at least one NTP (advantageously 1–3 NTPs), incubating this mixture under conditions which allow the at least one nucleic acid ligase to be active and quantitating the amount of nucleic acid in the sample by detecting and/or quantitating the amount of the at least one detectable species or the amount of the at least one binding species.

This invention also includes a method for the detection and/or quantitation of nucleic acid in a sample, which comprises; mixing at least one labeled random primer (advantageously one or two primers) at least 4 nucleotides in length (advantageously 6–10 in length) having at least one binding species (advantageously 1–3 binding species) and optionally at least one detectable species (advantageously 1–3 detectable species), with a sample nucleic acid, adding at least one nucleic acid ligase (advantageously 1–3 ligase), and at least one nucleic acid polymerase (advantageously 1–3 polymerase), adding at least one NTP (advantageously 3–5 NTPs), incubating this mixture under conditions which allow the at least one nucleic acid ligase and at least one nucleic acid polymerase to be active and quantitating the amount of nucleic acid in the sample by detecting and/or quantitating the amount of the at least one detectable species or the amount of the at least one binding species.

This invention also includes a kit comprising; a vial containing at least one random primer (advantageously one or two primers) at least 4 nucleotides in length (advantageously 6–10 in length) having at least one detectable species (advantageously 1–3 detectable species), and containing at least one NTP (advantageously 1–3 NTPs), having at least one binding species (advantageously 1–3 binding species) and optionally at least one NTP (advantageously 3–5 NTPs), a vial containing at least one nucleic acid polymerase and a vial containing at least one solid phase (advantageously 1–3 solid phases).

This invention also includes a kit comprising; a vial containing at least one random primer (advantageously one or two primers) at least 4 nucleotides in length (advantageously 6–10 in length) having at least one detectable species (advantageously 1–3 detectable species), a vial containing at least one NTP (advantageously 1–3 NTPs), having at least one binding species (advantageously 1–3 binding species) and optionally at least one NTP (advantageously 3–5 NTPs), a vial containing at least one nucleic acid polymerase and a vial containing at least one solid phase (advantageously 1–3 solid phases).

This invention also includes a kit comprising; a vial containing at least one random primer (advantageously one or two primers) at least 4 nucleotides in length (advantageously 6–10 in length) having at least one binding species (advantageously 1–3 binding species), and containing at least one NTP (advantageously 1–3 NTPs), having at least one detectable species (advantageously 1–3 detectable species), and optionally at least one NTP (advantageously 3–5 NTPs), a vial containing at least one nucleic acid polymerase and a vial containing at least one solid phase (advantageously 1–3 solid phases).

This invention also includes a kit comprising; a vial containing at least one random primer (advantageously one or two primers) at least 4 nucleotides in length (advantageously 6–10 in length) having at least one binding species (advantageously 1–3 binding species), a vial containing at least one NTP (advantageously 1–3 NTPs), having at least one detectable species (advantageously 1–3 detectable species), and optionally at least one NTP (advantageously 3–5 NTPs), a vial containing at least one nucleic acid polymerase and a vial containing at least one solid phase (advantageously 1–3 solid phases).

DETAILED DESCRIPTION OF THE INVENTION

The Tag-DNA assay of the subject invention improves on current methodology in several aspects. Tag-DNA assay is not as technically challenging or labor intensive compared to the assays currently used for detection of 10 pg amounts of DNA. Results from the assays that can accurately detect 10 pg of DNA have lengthy protocols (8 hrs–5 days) as compared to Tag-DNA assay (4 hrs). The Tag-DNA assay has a greater dynamic range for detection of DNA (5–10,000 pg) at a 60 minute reaction time than any of the current assays. The range of detecting greater amounts of DNA may be tailored to the requirements of the users by altering the enzyme incubation time. The subject assay can detect DNA larger than 100 base pairs regardless of base sequence or species of DNA. This is in contrast to slot-blot, which detects sequences that bind to the probe, or the threshold system which can only accurately detect DNA greater that 872 base pairs. Additionally, the generation of the signal in the Tag-DNA assay does not require radioactivity or incubation with a signal amplifier or enzyme substrate. Another advantage of the subject method is based on the ability to recount samples initially determined to be off the range of the standard curve. A sample will need to be re-run on slot-blot and threshold if a sample is out of the quantitation range of the standard curve. Thus, Tag-DNA improves on the speed and accuracy for determining the amount of DNA in the sample. Additionally, the results are generated faster due to the ease of the protocol and the short incubation time of the enzyme reaction.

The basic format for the assay of the subject invention is unique because the protocol utilizes an oligonucleotide having a detectable species (eg ruthenylated hexamer) as a primer for incorporating NTP(s) having a binding species (eg biotin-dNTP) as a capture moiety in a DNA template dependent manner. Specifically, random oligonucleotide hexamers covalently labeled with ruthenium at the 5' end are boiled and snapped-cooled in the presence of template DNA. DNA polymerase I (exonuclease Klenow fragment) is used to covalently incorporate biotin-dNTP, the capture moiety, directly to the ruthenylated-labeled hexamer. Free hexamers and biotin-dNTP are eliminated by a column purification step. The labeled DNA product is then captured using streptavidin coated magnetic beads and analyzed (eg using an ORIGEN analyzer, IGEN Inc.). Unknown concentrations of DNA are extrapolated from a standard curve generated by the Multicalc Wallac program using a 4 or 5 parameter logistic algorithm. Thus the assay of the subject invention not only detects low picogram amounts of DNA but also overcomes the disadvantages of current methodologies.

In addition to residual DNA detection, this assay format has a multitude of other potential application uses. One application is for the general quantitation of total DNA in the field of molecular biology. The methods currently available for determination of DNA are biased for specific bases. The assay of the subject invention does not discriminate between bases nor the origin or nature of the DNA (single vs. double stranded). Another format for random priming that has resulted in a signal differential involves use of polymerase to incorporate digoxygenin-dUTP onto a biotinylated random oligonucleotide hexamer which is detected by ruthenylated anti-digoxigenin antibody. Thus, the format described in this application can be adapted to a variety of molecular biology applications.

Detectable Species and Binding Species

A moiety or label is a binding species and/or a detectable species. Any binding species is also a detectable moiety as in the case of biotin or digoxigenin which can be a binding species and a detectable species. This is due to the ability of the binding species to be detected by binding another species which itself contains either a signal generating system or a directly detectable species. In certain cases the detectable species is not a binding species as in the case of a radioactive label, ie $^{32}p$ labeled at the 5' of the random primers. Thus, all binding species can be detectable species but not all detectable can be binding species. Those of ordinary skill in the art recognize that numerous possible detectable and binding species can be used in the present invention. Examples of binding species are biotin, avidin, streptavidin, antibodies, antigens, lectins, receptors, ligands, hormones, nucleic acid sequences, mimitopes, nucleic acid base pairing linear polymers (such as peptide nucleic acid, PNA). Examples of directly detectable species are radioactive molecules, fluorescent molecules, enzymes, electrochemiluminescent molecules, electrochemically active molecules, $Ru(bpy)_3^{2+}$, luminescent molecules, colored molecules, particles such as latex and colloidal gold.

Primers

Primers are polymer sequences capable of binding to nucleic acid sequences and directing the activity of nucleic acid template dependent enzymes such as polymerases, ligases, integrases, nucleases and recombinases in combination with nucleic acid templates. Primers are typically made synthetically to contain natural chemistries of the backbone and bases of nucleic acids. In addition to these synthetically made but natural nucleic acid sequences, modifications are commonly made to introduce moieties such as binding species for example biotin, digoxigenin, and also detectable moieties such as fluorescein, rhodamine, acridine, and $Ru(bpy)_3^{2+}$. Also the introduction of unnatural bases such as inosine, propyne dC, propyne dU, 5-bromo dC, 5-iodo dU, 5-fluoro dU, O-6 methyl dG, 7-deaza dG, N-6 methyl-2'-dA and additional modifications can be made which allow further chemistry such as introduction of amino and thiol groups within the sequence and at the ends of the sequences. It is also known that the primers need not be made only of naturally occurring bases and or backbone chemistries and that a number of unnatural chemistries have been used to make polymeric sequences which are able to bind to natural nucleic acid sequences. Some of these unnatural sequences are able to bind with greater affinity than the natural sequence as is the case of PNA (Perseptive biosystems, Framingham, Mass.) which is a peptide nucleic acid backbone. Typically in the case of these unnatural sequences they are not able to function as templates or primers in nucleic acid template dependent enzymatic reactions. They are able to function as primers when extended with a single natural base of nucleic acid. Thus these hybrid sequences of natural and unnatural elements are able to function as primers when combined with template and polymerases or ligase or other nucleic acid template dependent enzymes. It is also known that certain unnatural chemistries do not affect the ability of the primers to allow nucleic acid template dependent enzyme activities such as in the case of the phosphorothioate backbone chemistries which are able to activate RNases on hybridization to a RNA template. Examples of other alternative chemistries are available from various companies such as Oligo's etc, Wilsonville, Oreg. and Clontech, San Diego, Calif. Primers can also be made or isolated from biological sources such as calf thymus which is used as a source of DNA. Typically natural DNA is subjected to a fragmentation to generate a mixture of fragment lengths which are then fractionated to yield the desired primer lengths. One example of a fragmentation method is the use of a DNase I enzymatic reaction. Primers made in this way are considered to be random primers. These random primers can be from 4–400 bases long, advantageously 4–40 and most advantageously 6–10 bases long. Typically these random primers are from 4–100 bases long and may or may not include binding and/or detectable species. It is a advantageous embodiment of the present invention that the primer sequence is 5' $Ru(bpy)_3^{2+}$-(N)n, where n is 4–40 bases. Typically the primers of the present invention is 5' $Ru(bpy)_3^{2+}$-(N)n, where n is 6–10 bases.

Random primers are typically made synthetically by the use of mixtures of the four bases A, C, G, T (or U in place of T) during synthesis. This protocol results in a sequence of the formula 5'(N)n, where n=4–400, where N is A, C, G, T (or U in place of T). The random primer can contain elements in the linear polymer which are not random such as a labeling moiety ie $Ru(bpy)_3^{2+}$. Numerous modifications to the basic random primer core sequence can also be considered to be random primers. The types of modifications which can be considered are labeling with moieties as described above, the inclusion of unnatural bases as described above and also the use of un-natural backbone chemistries.

Solid Phases

Solid phases are used in numerous assay formats and are used as a means of capturing or binding complexes formed by the various binding species in the assay. This capture on to a solid phase is typically used as a means for separation of the specific complexes formed in an assay from the excess label species. This separation allows the detection of the specifically formed complexes in an assay. In a typical assay; for example an ELISA, the complex is captured directly on to the surface of a coated plastic tube and this tube is then washed to remove any excess enzyme label. Following this wash step the substrates are then added and the specific complex is detected and quantitated by the level of enzyme activity which is related to the level of color, fluorescence or luminescence generated by the action of the enzyme (label) used in this assay format. It is known that many solid phases can be used typically fibers, fibrils, plastic surfaces, plastic beads, magnetic beads, plastic tubes, gold surfaces, metal surfaces, metal beads, metal colloids, and other colloids.

Proximity Formats

In addition to the detection formats and assay formats described above which are based on the use of a solid phase to enable the analysis of formed complexes. Methods also exist for the detection of formed complexes which make use of the enhanced proximity of labels and binding species caused by the action of the template depended nucleic acid synthase enzymes of the present invention. Methods which make use of proximity to allow detection and quantitation are fluorescent energy transfer, scintillation proximity assay systems (Amersham, Dover, Del.), enzyme channeling assay systems (Litman et al (1980) Anal Chem, 106, 223), luminescent oxygen channeling assay systems (Ullman et al Clin Chem (1996) 42, 1518). These detection methods are also contemplated for the detection of nucleic acid using the methods of the invention to incorporate labels or binding species which are able to generate signals dependent on proximity of the incorporated groups into the products of the template dependent nucleic acid synthase enzymes.

Enzymes

The subject invention requires an enzyme which is active and activated by the presence of a primer and a template nucleic acid. Examples of such enzymes include, Taq DNA polymerase, T4 DNA polymerase, Klenow fragment (3'–5'), Pfu DNA polymerase, Exo-Pfu DNA polymerase, *E. coli* DNA polymerase I, Klenow fragment of DNA polymerase I, MMLV reverse transcriptase, AMV reverse transcriptase, Pfu DNA ligase, T4 DNA ligase, Taq DNA ligase, T4 RNA ligase, and *E. coli* DNA ligase. The conditions which are required for the optimal activity of these enzymes is well known to the art and buffers which support the activity of the these enzymes is typically supplied with the enzymes from the suppliers. In this invention activity of the polymerase enzymes is the incorporation of NTP's in a template dependent fashion not any of the other enzymatic activities of the polymerases such as various nuclease like activities such as 3'–5' exo-nuclease and 5'–3' exonuclease. Also in this invention activity of the ligase enzymes is the linkage of oligonucleotides in a template dependent fashion.

Buffers

The buffer conditions for the desired enzyme activities of the subject invention have an expected wide range. This is due to the wide variety of organisms with enzymes which have the desired properties of nucleic acid template dependent activity. In addition the use of polymerases, transcriptases and ligases with differing enzymatic systems and substrates also allows for a great variety of buffer conditions within the scope of the subject invention. These enzymes are well documented by the various vendors and in the literature regarding the potential scope of buffer conditions under which the enzymes of the subject inventions are active. For example the pH may be between 5.5 and 9.5, the NTP concentrations may vary from 1 pM to 10 mM. In the case of the $Mg^{2+}$ ion concentration the range is also wide from 0.05 mM and 500 mM and with certain enzymes the Mg ion can be replaced with Mn. Many enzymes like to have a reducing agent (eg DTT and/or 2-mercaptoethanol) present to maintain full activity for longer incubations the concentration can range from 0 to 500 mM. Also the sum of the molarities for the nucleic acid template dependent enzymes can be between 1 mM and 600 mM this can be made up only of the pH buffer, Mg salts, NTPs and reducing agents but may typically contain other salts (eg NaCl and/or KCl) to raise the ionic strength of the buffer.

Test Samples

The present invention provides a method for the detection and quantitation of nucleic acids using random primers. The nucleic acid of the present invention includes DNA, RNA in both single stranded from and double stranded forms. In an advantageous embodiment, the nucleic acid is DNA. These nucleic acids can be synthetic or natural, ie derived from a living organisms and viruses. The nucleic acid detectable by these methods are from 4 nucleotides or longer. There is no upper limit to the size of nucleic acids detectable using the present invention. In an advantageous embodiment, the size of the nucleic acid is at least 50 nucleotides.

Typically the nucleic acid to be detected is present in a biological samples or material derived from a biological source such as an organism, a fermentation, a culture, a plant, an animal, cells. Other examples of biological samples are cells, organs, tissues, body parts, to biological fluids. Examples of biological fluids are culture media, a fermentation, blood, mucous, urine, plasma, and saliva. In an advantageous embodiment, the sample is a purified biological sample intended for use as a pharmaceutical for example human growth hormone, insulin, G-CSF etc.

Assay Formats

Detection of DNA Using Primers with a Detectable Species

In one embodiment of the present invention random primers containing a detectable species, are added to purified samples with unknown levels of DNA. This mixture is then heated to denature the DNA followed by an annealing step which allows the primers to hybridize to the sample DNA. Following this step, the polymerase buffer is added which includes nucleotide triphosphates at least one of which is labeled with a moiety which is a binding species. A DNA dependent polymerase is then added. This mixture is then incubated to allow the polymerase to extend the primers in a template dependent manner which results in the incorporation of labeled NTPs into a primer extended product which has copied the sample DNA in a template dependent fashion. The resultant product of the polymerase extension of the primer has now covalently linked the detectable moiety of the primer to the binding moiety linked to the NTPs. This product of the primer, NTP polymerase reaction is then captured on to a solid phase and the detectable moiety is then detected. The level of the detectable moiety is then used to determine the level of DNA in the samples.

Detection of RNA Using Primers with a Detectable Species and Reverse Transcriptases In another embodiment of the present invention, random primers containing a detectable species, is added to purified samples with unknown levels of RNA. This mixture is heated to denature the RNA followed by an annealing step which allows the primers to hybridize to the sample RNA. Following this step, reverse transcriptase buffer is added which includes nucleotide triphosphates at least one of which is labeled with a moiety which is a binding species. A reverse transcriptase is then added. This mixture is then incubated to allow the polymerase to extend the primers in a template dependent manner which results in the incorporation of labeled NTPs into a primer extended product which has copied the sample RNA in a template dependent fashion. The resultant product of the reverse transcriptase extension of the primer has now covalently linked the detectable moiety of the primer to the binding moiety linked to the NTPs. This product of the primer, NTP reverse transcriptase reaction is then captured on to a solid phase and the detectable moiety is then detected. The level of the detectable moiety is then used to determine the level of RNA in the samples.

Detection of DNA Using Primers with a Binding Species and DNA Polymerases

In another embodiment of the present invention, random primers containing a binding species, is added to purified samples with unknown levels of DNA. This mixture is heated to denature the DNA followed by an annealing step which allows the primers to hybridize to the sample DNA. Following this step, the polymerase buffer is added which includes nucleotide triphosphates at least one of which is labeled with a moiety which is detectable. A DNA dependent polymerase is then added. This mixture is then incubated to allow the polymerase to extend the primers in a template dependent manner which results in the incorporation of labeled NTPs into a primer extended product which has copied the sample DNA in a template dependent fashion. The resultant product of the polymerase extension of the primer has now covalently linked the binding moiety of the primer to the detectable moiety linked to the NTPs. This product of the primer, NTP polymerase reaction is then captured on to a solid phase and the detectable moiety is then detected. The level of the detectable moiety is then used to determine the level of DNA in the samples.

Detection of DNA Using Primers and DNA Polymerases

In another embodiment of the present invention, random unlabeled primers are added to purified samples with unknown levels of DNA. This mixture is heated to denature the DNA followed by an annealing step which allows the primers to hybridize to the sample DNA. Following this step the polymerase buffer is added which includes nucleotide triphosphates at least one of which is labeled with a moiety which is detectable and at least one of which is labeled with a moiety which is a binding species and a DNA dependent polymerase. This mixture is then incubated to allow the polymerase to extend the primers in a template dependent manner which results in the incorporation of labeled NTPs into a primer extended product which has copied the sample DNA in a template dependent fashion. The resultant product of the polymerase extension of the primer has now covalently linked the binding moiety of the NTPs to the detectable moiety linked to the NTPs. This product of the primer, NTPs and polymerase reaction is then captured on to a solid phase and the detectable moiety is then detected. The level of the detectable moiety is then used to determine the level of DNA in the samples.

Detection of DNA Using Primers with a Detectable Species and DNA Ligases

In another embodiment of the present invention, random primers labeled with a binding species at the 5' end of the sequence, and random primers labeled with a moiety which is a detectable species at the 3' end of the sequence are added to purified samples with unknown levels of DNA. This mixture is heated to denature the DNA followed by an annealing step which allows the primers to hybridize to the sample DNA. Following this step the ligase buffer and a DNA dependent ligase are added. This mixture is then incubated to allow the ligase to ligate the primers in a template dependent manner which results in the covalent linkage of the labeled primers in a template dependent fashion. The resultant product of the ligase reaction covalently linked the binding moiety of one primer to the detectable moiety linked to the other primer. This product of the primer, ligase reaction is then captured on to a solid phase and the detectable moiety is then detected. The level of the detectable moiety is then used to determine the level of DNA in the samples. In this format DNA polymerase may also be used with the DNA ligases.

Detection of DNA Using Primers with $Ru(bpy)_3^{2+}$

In an advantageous embodiment of the present invention, random hexamer primers labeled with an ECL label of the formula 5' $Ru(bpy)_3^{2+}$-(N)6, is added to purified samples with unknown levels of DNA. This mixture is heated to denature the DNA followed by an annealing step which allows the primers to hybridize to the sample DNA. Following this step the polymerase buffer is added which includes a mixture of dNTPs, including at least one biotin-dNTP and klenow polymerase. This mixture is then incubated to allow the klenow polymerase to extend the primers in a template dependent manner which results in the incorporation of biotin-dNTPs into a primer extended product which has copied the sample DNA in a template dependent fashion. The resultant product of the polymerase extension of the primer has now covalently linked the 5' $Ru(bpy)_3^{2+}$-

(N)n, where n=6–36, primer to the biotin-NTPs. This product of the primer, NTP polymerase reaction is then captured on to a streptavidin bead and analyzed in an ORIGEN analyzer (IGEN, Gaithersburg, Md.). The signal detected is then used to determine the level of DNA in the samples based on a standard curve generated using known amounts of DNA in the above assay protocol.

It will be understood by those skilled in the art that these embodiments can be extended to other methods which still fall within the scope of the invention which is based on the use of a nucleic acid template dependent enzyme in combination with a primer to generate a molecular species via the action of the enzyme which is dependent on the levels of nucleic acid in the sample.

EXAMPLES

Example 1
Random Oligonucleotide Priming Using Poly A or Biotin Labeled Hexamers Random hexamers are oligonucleotides (NNNNNN) that are synthesized in a random fashion with respect to sequence order. The last nucleotide placed on by the synthesizer can be a dNTP that is modified. Modifications include a fluoresceinated, biotinylated or ruthenylated containing moiety. Several different forms of random hexamers were evaluated in order to determine the best format for hexamers for detecting low picogram amounts of DNA.

A. Random oligonucleotide hexamers containing a poly A sequence—Random oligonucleotide hexamers containing a poly A sequence $((A)_n$-NNNNNN) were utilized as template for DNA polymerase to incorporate biotin-dNTP into DNA. The product was captured by oligo-dT magnetic beads and the signal generated by a ruthenylated anti-biotin antibody or ruthenylated streptavidin. Alternatively, digoxigenin-dNTP was incorporated and the signal generated by a ruthenylated anti-digoxigenin antibody. Both permutations generated a signal that detects nanogram amounts of DNA.

B. Random oligonucleotide hexamers labeled with biotin were utilized as a primer for DNA polymerase to incorporate digoxigenin-dNTP into the template DNA. The labeled DNA was captured by streptavidin beads and the signal generated by a ruthenylated anti-digoxigenin antibody. These experiments showed that 100 ng DNA yielded a 100 fold increase in signal over background. A significant signal differential was evident by this random priming format.

C.

Example 2
Random Oligonucleotide Priming Using Ruthenylated Labeled Hexamers.

The ruthenium moiety is added to the hexamer by means of phosphoramidite chemistry. The ruthenium is the moiety that generates the electrochemoluminescent signal detected by the ORIGEN analyzer.

A. Annealing Conditions. Random oligonucleotide priming with ruthenylated hexamers was evaluated using different conditions for annealing hexamers to DNA. Using assay format 1 and 2 did not result in a significant difference between positive and negative control.

1. Target DNA was boiled and snap-cooled on ice. Biotin-ddUTP and the hexamer was then added and extended with exonuclease containing klenow fragment.

2. Target DNA was boiled with hexamers then slowly cooled to room temperature. Biotin-ddUTP was incorporated into the annealed hybrid during the polymerase reaction.

3. DNA diluted in water was boiled and snap-cooled with the ruthenylated hexamers. Biotin-dNTPs and biotin-ddUTP's were incorporated by klenow as the capture moiety. This assay format resulted in 100 fold signal differential between 4 ng and negative control. Although inclusion of manganese increases the polymerase affinity for ddNTP, the signal differential was significantly reduced. Therefore, use of ddUTP was eliminated and the biotin-dNTP in the reaction mix was the only biotin species used for the assay. This assay format resulted in 200 fold differential between negative control and 10 ng of target DNA. A standard curve was generated from target DNA in order to determine the sensitivity of this assay format. Picogram sensitivity was obtained only when the ruthenylated hexamers are added directly to each standard.

4. Taq-polymerase was tested using 10 uM dNTP (30% biotin-ATP). Use of PCR amplification of DNA with taq-polymerase resulted in a 1.5X signal differential with 10 pg of DNA.

Out of the four different permutations, # 3 was selected because of the potential for detecting low picogram amounts of target DNA. In addition to ruthenylated hexamers, ruthenylated random oligonucleotide decamers and octamers were also evaluated using this assay format. The results from these experiments did not yield a signal differential comparable to the hexamer.

B. Determination of the Concentration of Ruthenylated Hexamers. The ruthenylated hexamers were procured from Midland Certified Reagent Company (Midland, Tex.). The concentration of ruthenylated hexamer is determined using the extinction coefficient of ruthenium at 455 nm. (13,700). The stock hexamer was aliquoted at 10 ug/ul and stored at −20° C. Prior to use, the ruthenylated hexamers were diluted in 1 mM Tris-HCL (pH8) to a final concentration of 2 ug/ul.

C. Titration of the Ruthenylated Hexamers. Several experiments were performed to decrease the background signal. The concentration of hexamer was tested at three different concentrations (0.5,1, 1.5 and 2 ug/reaction) in order to determine the lowest concentration of hexamer that would not interfere with the signal differential. Out of all the different lots of hexamers used for this assay, lug of hexamer per reaction has been consistently showing the best signal differential. Hexamers that were not HPLC purified were compared to HPLC purified hexamers. These experiments showed that HPLC purification altered the characteristics of the assay and therefore non-HPLC purified hexamers were selected for the assay.

Example 3
Decreasing the Annealing Stringency Between Hexamer and DNA

The annealing of template DNA to the hexamer was initially performed in water. In order to increase the binding of hexamer to the template DNA, several salts were tested including 2X klenow buffer, NaCl, LiCl, 100 mM Tris-HCl (pH 7.5 or 9), 1 mM Hepes (pH6.6) and dextran sulfate. Compared to water, Tris-HCl (1 mM, pH 8) yielded the most consistent differential between picogram amounts of DNA and the negative control.

Example 4
Selection of DNA Polymerase, Optimal Concentration of dNTP and Percentage of Biotin-dNTP Normal random oligonucleotide priming methodologies function by extending the hexamers and copying the template DNA in the presence of labeled dNTPs. Several polymerases were tested for use in the Tag-DNA assay:

A. Taq-polymerase was tested using 200 uM dNTP (30% biotin-ATP). PCR was implemented to amplify target DNA with taq-polymerase. These results yielded a 1.5X signal differential with 10 pg of DNA.

B. In the early stages of assay development, the exonuclease containing and deficient klenow DNA polymerase enzymes were tested. As stated in the background, this activity is responsible for replacing the incorporated biotin-dNTP with unmodified dNTP. The best signal differential was generated using the 3'–5' exonuclease deficient klenow fragment because of the lack of proofreading activity. The signal differential with exonuclease containing enzyme was 24 fold whereas the exonuclease deficient enzyme gave a 66 fold differential with 5 ng of target DNA. Therefore, exonuclease deficient enzyme was selected for further use in the Tag-DNA assay.

C. The optimal dNTP concentration for the klenow fragment was selected (8 $\mu$M). This was determined on experimental evaluation of several different concentrations of biotin-dNTP. The percent biotin-dNTP represents both biotin-dATP and biotin-dCTP. Using 5 ng of target DNA yielded the following results:

| Condition | ECL Counts |
|---|---|
| Negative control | 4393 |
| 50% | 1411475 |
| 30% | 1820840 |
| 10% | 1280735 |
| 5% | 551261 |

A. The percent of biotin-dNTP was determined as the concentration that gave the best signal differential between negative control and 10 pg of target DNA. The concentrations for the 10X dNTP mix are as follows:

| | Stock | $\mu$L | Final ($\mu$M) | Source |
|---|---|---|---|---|
| dATP | 10 mM | 5.6 | 56 | Gibco/BRL (Gaithersburg, MD) |
| dGTP | 10 mM | 8 | 80 | Gibco/BRL (Gaithersburg, MD) |
| dTTP | 10 mM | 8 | 80 | Gibco/BRL (Gaithersburg, MD) |
| dCTP | 10 mM | 5.6 | 56 | Gibco/BRL (Gaithersburg, MD) |
| biotin-dATP | 400 $\mu$M | 60 | 24 | Gibco/BRL (Gaithersburg, MD) |
| biotin-dCTP | 400 $\mu$M | 60 | 24 | Gibco/BRL (Gaithersburg, MD) |
| DEPC water | | 852.8 | | Ambion |

Example 5
Kinetic Properties of Exonuclease Deficient Klenow DNA Polymerase in Random Priming Reactions With Ruthenylated Hexamers In order to determine the highest sensitivity for quantitating picogram amounts of DNA, kinetic analysis was performed. These results suggested that the signal differential between negative control and 5 pg of DNA increases with longer incubation times. Furthermore, these results further suggest that higher amounts of DNA can be quantitated using this format. Because the goal was to develop an assay that detects low picogram amounts of DNA, the assay detailed in this protocol focuses on characterization of the 60 minute assay.

| | Mean Counts from ORIGEN Analyzer | | | |
|---|---|---|---|---|
| pg DNA | 30 minutes | 60 minutes | 120 minutes | 240 minutes |
| 500,000 | 13294384 | out of range | out of range | out of range |
| 250,000 | 16394352 | out of range | out of range | out of range |
| 125,000 | 15241295 | out of range | out of range | out of range |
| 31,000 | 12908362 | 17215729 | out of range | out of range |
| 16,000 | 6764104 | 10647597 | 13249103 | out of range |
| 5,000 | 4394376 | 6886864 | 9635308 | 14839843 |
| 500 | 397842 | 922998 | 1560462 | 3672890 |
| 100 | 120605 | 210523 | 394444 | 945501 |
| 50 | 60912 | 100712 | 159976 | 416124 |
| 10 | 22628 | 36665 | 62114 | 129247 |
| 5 | 19005 | 27164 | 43696 | 89136 |
| 0 | 14881 | 21477 | 26819 | 18982 |

Example 6
Elimination of Ruthenylated Hexamers Not Extended by the DNA Polymerase In order to maximize the signal to noise ratio between low picogram amounts of DNA and the negative control, there is a requirement for elimination of the ruthenylated hexamers. Elimination of the column step increases the signal from the negative control and therefore decreases the assay sensitivity. Several blocking agents such as (Denhart's, BSA, CHAPS, Tween-20 and assay diluent) did not efficiently block the background contributed by the ruthenylated hexamers. These results confirmed the requirement for a column purification step in the quantitation of low picogram amounts of target DNA. Quantitation of higher amounts of target DNA worked well using this format. Experiments also showed that Boeringer-Mannheim columns were advantageous for determining low picogram amounts of DNA as compared to other commercially available columns.

Example 7
Preparation of Samples for Tag-DNA Assay

In order to identify the most efficient protocol for extracting small quantities of DNA from high protein samples, two DNA extraction kits were evaluated; WAKO and Puregene. Using several different mock buffers containing 70 mg/ml of BSA, the performance of these extraction protocols in the Tag-DNA assay was determined. In addition to glycogen, another co-precipitant (pellet paint; Novagen) to increase the yield of low picogram quantities of DNA was utilized. An additional wash step with 70% ethanol was also implemented to eliminate matrix interferences in the assay. The results from these experiments suggested that the WAKO kit works best not only to eliminate protein from sample but also to yield close to 100% recovery of the DNA from samples with low picogram amounts of DNA. Using this protocol, a large white precipitate that is not eliminated during wash steps and/or ethanol in sample prior to testing in the assay was observed to interfere with the generation of the signal.

Example 8
Tag-DNA Assay Protocol

The protocol described in this example is for duplicate determinations made as a 3X solution. Hexamers at 2 $\mu$g/$\mu$L (0.5 $\mu$L/reaction or 1.5 $\mu$L/3X reactions; example 2) were aliquoted into siliconized tubes. Negative control [1 mM Tris-HCl (pH8)], DNA standards and samples (5 $\mu$L/reaction or 15 $\mu$L/3X reactions) were aliquoted into separate siliconized tubes, immediately capped, vortexed and centrifuged. The DNA standards are aliquoted from the lowest to highest concentration. The hexamer was annealed to the DNA by boiling the tubes at 100° C. for 3 minutes, and immediately followed by snap cooling on ice for 5 minutes.

A master mix of the following components was prepared according to the number of reactions in the experiment as detailed in the following table:

| Master Mix (1 X) | | |
|---|---|---|
| DEPC Water | 1.5 μL | |
| dNTP Mix | 1.0 μL | Described example 3 |
| 10X Klenow Buffer | 1.0 μL | New England Biolabs |
| Klenow (exonuclease-) | 1.0 μL | New England Biolabs |

The master mix (4.5 μL) is aliquoted into a new set of reaction tubes. The negative control, DNA standards, QC standards and samples (5.5 μL/reaction) were aliquoted into the PCR tubes containing the master mix and the reaction was allowed to incubate 60 minutes at 25° C. After incubation the biotin-dNTPs and the unextended and <100 basepair extended tag-hexamers were eliminated using the Boehringer Mannheim High Pure PCR purification columns according to manufacturers instructions (see example 7). Following incubation, 200 μL of column binding buffer was added to each tube and applied to the column. The column was washed with 500 ul of wash buffer and the sample was eluted using 200 ul of elution buffer or 1XTE. The sample was then transferred to analyzer tubes and the product bound to streptavidin beads (100 ul of 0.1 mg/ml diluted in PBS-1; IGEN, Inc.) by a 30 minute incubation at room temperature while vortexing. The relative ECL counts were subsequently obtained on an ORIGEN analyzer.

Example 9

Quantitation of DNA and Preparation of DNA Standards

A. Preparation of DNA standards: The concentration of the standard sheared calf thymus DNA (Gibco/BRL) was determined by optical density to be 9.3 ug/ul. This concentration was used to generate the standard curve by diluting DNA in 1 mM Tris (pH8) (Ambion). The dilution scheme is as follows:

| Tube # | DNA Source | Vol. DNA (μL) | Vol. Tris (μL) | Final [DNA] | [DNA] in Std. |
|---|---|---|---|---|---|
| B | 100 ng/μL | | | 100 ng/μL | 500 ng |
| 2 | 100 ng/μL | 10 | 490 | 2 ng/μL | 10 ng |
| 3 | 2 ng/μL | 250 | 250 | 1 n/μL | 5 ng |
| 4 | 1 ng/μL | 100 | 400 | 200 pg/μL | 1 ng |
| 5 | 200 pg/μL | 250 | 250 | 100 pg/μL | 500 pg |
| 6 | 100 pg/μL | 100 | 400 | 20 pg/μL | 100 pg |
| 7 | 20 pg/μL | 250 | 250 | 10 pg/μL | 50 pg |
| 8 | 10 pg/μL | 100 | 400 | 2 pg/μL | 10 pg |
| 9 | 2 pg/μL | 250 | 250 | 1 pg/μL | 5 pg |
| 10 | 1 pg/μL | 100 | 400 | 0.2 pg/μL | 1 pg |
| blank | none | 0 | 500 | 0 | 0 |

| DNA Quality Controls | | | | |
|---|---|---|---|---|
| Tube | DNA Source | DNA (ul) | 1 mM Tris (ul) | DNA concentration | DNA/reaction |
| QC1 | 6000 pg/ul | 10 | 90 | 600 pg/ul | 3000 pg |
| QC2 | 600 pg/ul | 10 | 90 | 60 pg/ul | 300 pg |
| QC3 | 60 pg/ul | 10 | 490 | 1.2 pg/ul | 6 pg |

B. Determination of DNA. In order to eliminate any bias due to base composition, the fluorescence of ethidium bromide was selected as the means to accurately determine the concentration of all DNAs studied including DNA fragments. The relative amount of DNA in the sample is extrapolated from a standard curve generated by using sheared calf thymus DNA standard curve. The basic protocol used for these determinations follows the protocol outlined in the current protocols.

Standards generated from calf thymus DNA resulted in the following values. The curve generated from these values was back-fitted to determine the goodness of fit of the curve. It is evident that the curve generated from these data can accurately determine DNA concentrations as low as 5 pg of DNA. This assay has also been carried out using Dynal M280 beads coated with streptavidin with similar results.

| pg DNA | Back-fitted value | Mean ECL counts |
|---|---|---|
| 5 | 5.0 | 23921 |
| 10 | 8.981 | 33021 |
| 50 | 41.45 | 96404 |
| 100 | 101.1 | 196644 |
| 500 | 453 | 682223 |
| 1000 | 8553 | 1148437 |
| 5000 | 4929 | 4323320 |
| 10000 | 10012 | 6721160 |

Example 10

Comparison to Slot-Blot and Threshold Methodologies

Several samples were obtained and extracted using Wako extraction. Comparative assay results are shown below:

| Sample | Threshold pg DNA/ml | Slot-blot pg DNA/ml | Tag-DNA pg DNA/ml |
|---|---|---|---|
| 1 | 1,300,000 | — | 1,271,000 |
| 2 | 20,000 | — | 59,000 |
| 3 | 736,000 | — | 1,247,000 |
| 4 | — | 380 | 660 |
| 5 | — | 400 | 720 |
| 6 | — | 440 | 670 |
| 7 | — | 620 | 1040 |

Example 11

Sensitivity of the Tag-DNA Assay for all DNAs Regardless of Size and Species

Whether DNA from other species behaved similar to that observed with calf thymus DNA was evaluated. The genomic DNA from all species studied have a unique DNA size and composition. It is evident that mouse DNA generates a standard curve similar to that seen with the calf thymus DNA:

| pg mouse DNA | Back-fitted value | Mean ECL counts |
|---|---|---|
| 5 | 6 | 28599 |
| 10 | 10 | 36123 |
| 50 | 47 | 102272 |
| 100 | 116 | 218254 |
| 500 | 491 | 778042 |
| 1000 | 955 | 1369470 |
| 5000 | 4708 | 4269472 |
| 10000 | 11722 | 6507011 |

The concentration of E. coli DNA (average size 5 kb) was determined as described in Example 2 using ethidium bromide fluorescence spectroscopy and tested in the tag-DNA assay. This experiment shows that DNA from species other than mammalian are efficiently detected in the Tag-DNA assay.

| DNA (pg) | Calf Thymus | S. Cervicie (50 kb) | Mouse | E. coli (5 kb) |
|---|---|---|---|---|
| 5 | 5 | 4 | 7 | 4 |
| 10 | 10 | 7 | 10 | 11 |
| 50 | 50 | 70 | 45 | 56 |
| 100 | 97 | 135 | 115 | 118 |
| 500 | 506 | 553 | 533 | 512 |
| 1000 | 995 | 1007 | 1068 | 979 |
| 5000 | 498 | 3522 | 4897 | — |
| 10000 | 10376 | — | 9481 | — |

Whether this assay detected smaller fragments of DNA was evaluated. Specific PCR generated products were quantitated by ethidium bromide fluorescence and tested in the assay. The relative concentration of DNA in the PCR products are extrapolated from the calf thymus standard curve.

A range of DNA fragments isolated from an agarose gel was tested in the assay.

| Range of basepairs | |
|---|---|
| 200–300 | 117 |
| 300–400 | 127 |
| 400–500 | 96 |
| Cald Thymus | 110 |

The back-fitted values obtained from calf thymus DNA standard curve suggests that the assay does not discriminate based on size or sequence.

While the present invention has been described in terms of specific examples and compositions, it is understood that based on the information contained within this invention variations and modifications will occur to those skilled in the art.

What is claimed is:

1. A method for determining total nucleic acid in a sample, which comprises:
   a) mixing at least one random primer at least 4 nucleotides in length, having at least one detectable species with a sample which may contain nucleic acid,
   b) adding at least one nucleotide triphosphate having at least one binding species and optionally at least one second nucleotide triphosphate,
   c) adding at least one nucleic acid polymerase,
   d) incubating the mixture of step c), under conditions which allow said at least one nucleic acid polymerase to be active,
   e) contacting the mixture of step d) with at least one solid phase,
   f) measuring total nucleic acid in said sample by measuring the total amount of said at least one detectable species bound to said solid phase, and
   g) determining whether the total nucleic acid in said sample is higher or lower than a threshold amount of contamination, wherein the threshold amount of contamination is equal to or less than 100 pg.

2. A method for determining total nucleic acid in a sample, which comprises:
   a) mixing at least one random primer at least 4 nucleotides in length, having at least one binding species with a sample which may contain nucleic acid
   b) adding at least one nucleotide triphosphate having at least one detectable species and optionally at least one second nucleotide triphosphate,
   c) adding at least one nucleic acid polymerase,
   d) incubating the mixture of step c), under conditions which allow said at least one nucleic acid polymerase to be active,
   e) contacting the mixture of step d) with at least one solid phase,
   f) measuring total nucleic acid in said sample by measuring the total amount of said at least one detectable species bound to said solid phase, and
   g) determining whether the total nucleic acid in said sample is higher or lower than a threshold amount of contamination, wherein the threshold amount of contamination is equal to or less than 100 pg.

3. A method for determining total nucleic acid in a sample, which comprises:
   a) mixing at least one random primer at least 4 nucleotides in length with a sample which may contain nucleic acid,
   b) adding at least one nucleotide triphosphate having at least one binding species and optionally at least one nucleotide triphosphate having at least one detectable species and optionally at least one second nucleotide triphosphate,
   c) adding at least one nucleic acid polymerase,
   d) incubating the mixture of step c), under conditions which allow said at least one nucleic acid polymerase to be active,
   e) contacting the mixture of step d) with at least one solid phase,
   f) measuring total nucleic acid in said sample by measuring the total amount of said at least one detectable species or the amount of said at least one binding species bound to said solid phase, and
   g) determining whether the total nucleic acid in said sample is higher or lower than a threshold amount of contamination, wherein the threshold amount of contamination is equal to or less than 100 pg.

4. A method for determining total nucleic acid in a sample, which comprises:
   a) mixing at least one first labeled random primer at least 4 nucleotides in length having at least one binding species and at least one second random primer at least 4 nucleotides in length having at least one detectable species, with a sample which may contain nucleic acid,
   b) adding at least one nucleic acid ligase,
   c) incubating the mixture of step b), under conditions which allow said at least one nucleic acid ligase to be active, d) contacting the mixture of step c) with at least one solid phase, e) measuring total nucleic acid in said sample by measuring the total amount of said at least one detectable species or the amount of said at least one binding species bound to said solid phase, and f) determining whether the total nucleic acid in said sample is higher or lower than a threshold amount of contamination, wherein the threshold amount of contamination is equal to or less than 100 pg.

5. A method for determining total nucleic acid in a sample, which comprises:

a) mixing at least one first labeled random primer at least 4 nucleotides in length having at least one binding species and at least one second random primer at least 4 nucleotides in length having at least one detectable species, with a sample which may contain nucleic acid, b) adding at least one nucleic acid ligase and at least one nucleic acid polymerase, c) incubating the mixture of step b), under conditions which allow said at least one nucleic acid ligase and at least one nucleic acid polymerase to be active, d) contacting the mixture of step c) with at least one solid phase, e) measuring total nucleic acid in said sample by measuring the total amount of said at least one detectable species or the amount of said at least one binding bound to said solid phase, and f) determining whether the total nucleic acid in said sample is higher or lower than a threshold amount of contamination, wherein the threshold amount of contamination is equal to or less than 100 pg.

6. A method as in claim 1, wherein said at least one binding species is selected from the group consisting of biotin, avidin, streptavidin, antibody, antigen, lectin, receptor, ligand, hormone, nucleic acid sequence, mimitope and nucleic acid base pairing polymer.

7. A method as in claim 1, wherein said at least one detectable species is selected from the group consisting of biotin, avidin, streptavidin, antibody, antigen, lectin, receptor, ligand, hormone, nucleic acid sequence, mimitope, nucleic acid base pairing polymer, fluorescent molecule, electrochemiluminescent molecule, radioactive molecule, colored molecule, peroxidase, alkaline phosphatase and enzymes capable of producing a detectable species.

8. A method as in claim 1, wherein said at least one nucleic acid polymerase is selected from the group consisting of Taq DNA polymerase, T4 DNA polymerase, Klenow fragment, Pfu DNA polymerase, Exo-Pfu DNA polymerase, E. coli DNA polymerase I, Klenow fragment of DNA polymerase I, MMLV reverse transcriptase and AMV reverse transcriptase.

9. A method as in claim 1, wherein said at least one solid phase is selected from the group consisting of fiber, fibril, plastic surface, plastic bead, magnetic bead, plastic tube, gold surface, metal surface, metal bead and colloids.

10. A method as in claim 1, wherein said at least one nucleotide triphosphate is selected from the group consisting of dATP, dGTP, dCTP, dUTP, dTTP, ATP, CTP, GTP, TTP, UTP inosineTP, propyne dCTP, propyne dUTP, 5-bromo dCTP, 5-iodo dUTP, 5-fluoro dUTP, O-6 methyl dGTP, 7-deaza dGTP, N-6 methyl-2'-dATP, biotin-dATP, biotin-dCTP, biotin-dUTP, digoxigenin dUTP, digoxigenin UTP and biotin ddUTP.

11. A method as in claim 1, wherein said at least one random primer is 4–70 nucleotides.

12. A method as in claim 1, wherein said conditions comprise a solution with a pH between 5.5 and 9.5, a nucleotide triphosphate concentration between 1 pM and 10 mM, a Mg2+ concentration between 0.05 mM and 500 mM, and a reducing agent concentration between 0 and 500 mM, wherein the sum of the molarities is between 1 mM and 500 mM.

13. A method as in claim 4, wherein said at least one ligase is selected from the group consisting of Pfu DNA ligase, T4 DNA ligase, Taq DNA ligase, T4 RNA ligase, and E. coli DNA ligase.

14. A method as in claim 1, wherein said random primer is from 4 to 20 nucleotides in length.

15. A method as in claim 14, wherein said at least one detectable species is selected from the group consisting of biotin, nucleic acid sequence, nucleic acid base pairing linear polymer, fluorescent molecule, electrochemiluminescent molecule, radioactive molecule, peroxidase and alkaline phosphatase.

16. A method as in claim 14, wherein said at least one binding species is selected from the group consisting of biotin, antigen, lectin, ligand, hormone, nucleic acid sequence, mimitope and nucleic acid base pairing linear polymer.

17. A method as in claim 14, wherein said at least one nucleic acid polymerase is selected from the group consisting of Taq DNA polymerase, Klenow fragment (3'–5') of E. coli DNA polymerase I and Klenow fragment of DNA polymerase I.

18. A method as in claim 14, wherein said at least one solid phase is selected from the group consisting of magnetic bead, plastic plate and polymer bead.

19. A method as in claim 14, wherein said at least one nucleotide triphosphate is selected from the group consisting of dATP, dGTP, dCTP, dUTP, dTTP, 7-deaza dGTP, biotin-dATP, biotin-dCTP, biotin-dUTP, digoxigenin dUTP, digoxigenin UTP and biotin ddUTP.

20. A method as in claim 14, wherein said random primer is 6–10 nucleotides in length.

21. A method as in claim 14, wherein said conditions comprise those optimal for Klenow fragment of DNA polymerase I to synthesize DNA.

22. A method as in claim 20, wherein said NTP is a dNTP.

23. A method for determining total nucleic acid in a sample, which comprises:

a) mixing at least one random primer at least 4 nucleotides in length having at least one detectable species, with a sample which may contain nucleic acid, b) adding at least one nucleotide triphosphate having at least one binding species and optionally at least one second nucleotide triphosphate, c) adding at least one nucleic acid polymerase, d) incubating the mixture of step c), under conditions which allow said at least one nucleic acid polymerase to be active, e) measuring total nucleic acid in said sample by measuring the total amount of said at least one detectable species or the amount of said at least one binding species, and f) determining whether the total nucleic acid in said sample is higher or lower than a threshold amount of contamination, wherein the threshold amount of contamination is equal to or less than 100 pg.

24. A method for determining total nucleic acid in a sample, which comprises:

a) mixing at least one random primer at least 4 nucleotides in length, having at least one binding species, with a sample which may contain nucleic acid, b) adding at least one nucleotide triphosphate having at least one detectable species and optionally at least one second nucleotide triphosphate, c) adding at least one nucleic acid polymerase, d) incubating the mixture of step c), under conditions which allow said at least one nucleic acid polymerase to be active e) measuring total nucleic acid in said sample by measuring the total amount of said at least one detectable species or the amount of said at least one binding species, and f) determining whether the total nucleic acid in said sample is higher or lower than a threshold amount of contamination, wherein the threshold amount of contamination is equal to or less than 100 pg.

25. A method for determining total nucleic acid in a sample, which comprises:

a) mixing at least one random primer at least 4 nucleotides in length with a sample which may contain nucleic acid, b) adding at least one nucleotide triphosphate having at least one binding moiety and optionally at least one second nucleotide triphosphate having at least one label and optionally at least one nucleotide triphosphate, c) adding at least one nucleic acid polymerase, d) incubating the mixture of step c), under conditions which allow said at least one nucleic acid polymerase to be active, e) measuring total nucleic acid in said sample by measuring the total amount of said at least one label or the amount of said at least one binding moiety, and f) determining whether the total nucleic acid in said sample is higher or lower than a threshold amount of contamination, wherein the threshold amount of contamination is equal to or less than 100 pg.

26. A method for determining total nucleic acid in a sample, which comprises:

a) mixing at least one labeled random primer at least 4 nucleotides in length having at least one binding species and optionally at least one second random primer at least 4 nucleotides in length having at least one detectable species, with a sample nucleic acid, b) adding at least one nucleic acid ligase, c) incubating the mixture of step b), under conditions which allow said at least one nucleic acid ligase to be active, d) measuring total nucleic acid in said sample by measuring the total amount of said at least one detectable species or the amount of said at least one binding species, and e) determining whether the total nucleic acid in said sample is higher or lower than a threshold amount of contamination, wherein the threshold amount of contamination is equal to or less than 100 pg.

27. A method for determining total nucleic acid in a sample, which comprises:

a) mixing at least one labeled random primer at least 4 nucleotides in length having at least one binding species and optionally at least one second random primer at least 4 nucleotides in length having at least one detectable species, with a sample which may contain nucleic acid, b) adding at least one nucleic acid ligase and at least one nucleic acid polymerase, c) adding at least one nucleotide triphosphate, d) incubating the mixture of step c), under conditions which allow said at least one nucleic acid ligase and at least one nucleic acid polymerase to be active, e) measuring total nucleic acid in said sample by measuring the total amount of said at least one detectable species or the amount of said at least one binding species, and f) determining whether the total nucleic acid in said sample is higher or lower than a threshold amount of contamination, wherein the threshold amount of contamination is equal to or less than 100 pg.

28. A method as in claim 23, wherein said at least one detectable species is selected from the group consisting of biotin, avidin, streptavidin, antibody, antigen, lectin, receptor, ligand, hormone, nucleic acid sequence, mimitope, nucleic acid base pairing linear polymer, fluorescent molecule, electrochemiluminescent molecule, radioactive molecule, colored molecule, peroxidase, alkaline phosphatase and enzymes capable of producing a detectable species.

29. A method as in claim 1, wherein said at least one nucleic acid polymerase is selected from the group consisting of Taq DNA polymerase, T4 DNA polymerase, Klenow fragment, Pfu DNA polymerase, Exo-Pfu DNA polymerase, E. coli DNA polymerase I, Klenow fragment of DNA polymerase I, MMLV reverse transcriptase and AMV reverse transcriptase.

30. A method as in claim 23, wherein said at least one nucleotide triphosphate is selected from the group consisting of dATP, dGTP, dCTP, dUTP, dTTP, ATP, CTP, GTP, TTP, UTP inosineTP, propyne dCTP, propyne dUTP, 5-bromo dCTP, 5-iodo dUTP, 5-fluoro dUTP, O-6 methyl dGTP, 7-deaza dGTP, N-6 methyl-2'-dATP, biotin-dATP, biotin-dCTP, biotin-dUTP, digoxigenin dUTP, digoxigenin UTP and biotin ddUTP.

31. A method as in claim 23, wherein said at least one random primer is 4–70 nucleotides.

32. A method as in claim 23, wherein said conditions comprise a solution with a pH between 5.5 and 9.5, a nucleotide triphosphate concentration between 1 pM and 10 mM, a Mg2+ concentration between 0.05 mM and 500 mM, and a reducing agent concentration between 0 and 500 mM, where the sum of the molarities is between 1 M and 500 mM.

33. A method as in claim 26, wherein said at least one ligase is selected from the group consisting of Pfu DNA ligase, T4 DNA ligase, Taq DNA ligase, T4 RNA ligase, and E. coli DNA ligase.

34. A method for determining total nucleic acid in a sample, which comprises:

a) mixing at least one random primer at least 4 nucleotides in length having at least one first label, with a sample nucleic acid, b) adding at least one nucleotide triphosphate having at least one second label and optionally at least one second nucleotide triphosphate, c) adding at least one nucleic acid polymerase, d) incubating the mixture of step c), under conditions which allow said at least one nucleic acid polymerase to be active, e) measuring total nucleic acid in said sample by measuring the total amount of said at least one first label or the amount of said at least one second label, and f) determining whether the total nucleic acid in said sample is higher or lower than a threshold amount of contamination, wherein the threshold amount of contamination is equal to or less than 100 pg.

35. A method for determining total nucleic acid in a sample, which comprises:
  a) mixing at least one labeled random primer at least 4 nucleotides in length having at least one first label species and optionally at least one second random primer at least 4 nucleotides in length having at least one second label, with a sample which may contain nucleic acid,
  b) adding at least one nucleic acid ligase,
  c) incubating the mixture of step b), under conditions which allow said at least one nucleic acid ligase to be active,
  d) measuring total nucleic acid in said sample by measuring the total amount of said at least one first label or the amount of said at least one second label, and
  e) determining whether the total nucleic acid in said sample is higher or lower than a threshold amount of contamination, wherein the threshold amount of contamination is equal to or less than 100 pg.

36. A method for determining total nucleic acid in a sample, which comprises:
  a) mixing at least one labeled random primer at least 4 nucleotides in length having at least one first label and optionally at least one second random primer at least 4 nucleotides in length having at least one second label, with a sample which may contain nucleic acid
  b) adding at least one nucleic acid ligase and at least one nucleic acid polymerase,
  c) adding at least one nucleotide triphosphate,
  d) incubating the mixture of step c), under conditions which allow said at least one nucleic acid ligase and at least one nucleic acid polymerase to be active,
  e) measuring total nucleic acid in said sample by measuring the total amount of said at least one first label or the amount of said at least one second label, and
  f) determining whether the total nucleic acid in said sample is higher or lower than a threshold amount of contamination, wherein the threshold amount of contamination is equal to or less than 100 pg.

37. The method of claim 1, wherein said method is capable of detecting total nucleic acid in amounts as low as 5 pg.

38. The method of claim 2, wherein said method is capable of detecting total nucleic acid in amounts as low as 5 pg.

39. The method of claim 3, wherein said method is capable of detecting total nucleic acid in amounts as low as 5 pg.

40. The method of claim 4, wherein said method is capable of detecting total nucleic acid in amounts as low as 5 pg.

41. The method of claim 5, wherein said method is capable of detecting total nucleic acid in amounts as low as 5 pg.

42. The method of claim 23, wherein said method is capable of detecting total nucleic acid in amounts as low as 5 pg.

43. The method of claim 24, wherein said method is capable of detecting total nucleic acid in amounts as low as 5 pg.

44. The method of claim 25, wherein said method is capable of detecting total nucleic acid in amounts as low as 5 pg.

45. The method of claim 26, wherein said method is capable of detecting total nucleic acid in amounts as low as 5 pg.

46. The method of claim 27, wherein said method is capable of detecting total nucleic acid in amounts as low as 5 pg.

47. The method of claim 34, wherein said method is capable of detecting total nucleic acid in amounts as low as 5 pg.

48. The method of claim 35, wherein said method is capable of detecting total nucleic acid in amounts as low as 5 pg.

49. The method of claim 36, wherein said method is capable of detecting total nucleic acid in amounts as low 5 pg.

50. The method of claim 1, wherein said method is capable of detecting DNA fragments shorter than 800 basepairs.

51. The method of claim 2, wherein said method is capable of detecting total DNA fragments shorter than 800 basepairs.

52. The method of claim 3, wherein said method is capable of detecting total DNA fragments shorter than 800 basepairs.

53. The method of claim 4, wherein said method is capable of detecting total DNA fragments shorter than 800 basepairs.

54. The method of claim 5, wherein said method is capable of detecting total DNA fragments shorter than 800 basepairs.

55. The method of claim 23, wherein said method is capable of detecting DNA fragments shorter than 800 basepairs.

56. The method of claim 24, wherein said method is capable of detecting DNA fragments shorter than 800 basepairs.

57. The method of claim 25, wherein said method is capable of detecting DNA fragments shorter than 800 basepairs.

58. The method of claim 26, wherein said method is capable of detecting DNA fragments shorter than 800 basepairs.

59. The method of claim 27, wherein said method is capable of detecting DNA fragments shorter than 800 basepairs.

60. The method of claim 34, wherein said method is capable of detecting DNA fragments shorter than 800 basepairs.

61. The method of claim 35, wherein said method is capable of detecting DNA fragments shorter than 800 basepairs.

62. The method of claim 36, wherein said method is capable of detecting DNA fragments shorter than 800 basepairs.

* * * * *

(12) EX PARTE REEXAMINATION CERTIFICATE (6579th)
United States Patent
Heroux et al.

(10) Number: US 6,635,418 C1
(45) Certificate Issued: *Dec. 23, 2008

(54) ASSAY METHODS FOR NUCLEIC ACID IN A SAMPLE

(75) Inventors: Jeffrey A. Heroux, Middletown, MD (US); Marta L. Corcoran, Rockville, MD (US); Savitha M. Rao, Gaithersburg, MD (US)

(73) Assignee: Bioveris Corporation, Gaithersburg, MD (US)

( * ) Notice: This patent issued on a continued prosecution application filed under 37 CFR 1.53(d), and is subject to the twenty year patent term provisions of 35 U.S.C. 154(a)(2).

Reexamination Request:
No. 90/008,164, Aug. 15, 2006

Reexamination Certificate for:
Patent No.: 6,635,418
Issued: Oct. 21, 2003
Appl. No.: 09/023,483
Filed: Feb. 13, 1998

(51) Int. Cl.
*C12Q 1/68* (2006.01)
*C12P 19/34* (2006.01)
*C07H 21/00* (2006.01)
*C07H 21/04* (2006.01)

(52) U.S. Cl. .................. 435/6; 435/91.2; 435/91.52; 435/91.51; 536/25.32; 536/25.6

(58) Field of Classification Search .................. None
See application file for complete search history.

(56) References Cited

U.S. PATENT DOCUMENTS

| | | | |
|---|---|---|---|
| 5,043,272 A | 8/1991 | Hartley | |
| 5,364,759 A | 11/1994 | Caskey et al. | |
| 5,413,906 A | 5/1995 | Eberle et al. | |
| 5,599,662 A | 2/1997 | Respess | |
| 6,096,499 A | 8/2000 | Kozlowski et al. | |

OTHER PUBLICATIONS

Kaczorowski et al. "Co–operativity of hexamer ligation," Gene 179: 189–193, 1996.*
Litman et al., "Enzyme Channelling Immunoassay: A New Homogeneous Enzyme Immunoassay Technique" Analytical Biochemistry, vol. 106, pp. 223–229 (1980).
Feinberg et al., "A Technique for Radiolabeling DNA Restriction Endonuclease Fragments to High Specific Activity" Analytical Biochemistry, vol. 132, pp. 6–13 (1983).
Wu et al., "The Litigation Amplification Reaction (LAR)–Amplification of Specific DNA Sequences Using Sequential Rounds of Template—Dependent Litigation" Genomics, vol. 4, pp. 560–569 (1989).
Briggs et al., "Quantitation of DNA and Protein Impurities in Biopharmaceuticals" Analytical Chemistry, vol. 63, pp. 850–859 (1991).
Merrick et al., "Threshold™ A Complete System for Quantitative Analysis of Total DNA, Protein Impurities and Relevant Proteins" Biotech Forum Europe, vol. 9, No. 6, pp. 398–403 (Jun. 1992).
Ullman et al., "Luminescent Oxygen Channelling Assay (LOCI™): Sensitive, Broadly Applicable Homogeneous Immunoassay Method" Clinical Chemistry, vol. 42, No. 9, pp. 1518–1526 (1996).
DiCesare et al., "A High–Sensitivity Electrochemiluminescence–Based Detection System for Automated PCR Product Quantitation" BioTechniques, vol. 15, No. 1, pp. 152–157 (1993).

* cited by examiner

*Primary Examiner*—Gary L Kunz

(57) ABSTRACT

The present invention relates to a method for the determination of the presence and amount of DNA in a sample. The method is based on the use of a nucleic acid template dependent enzyme in combination with a random primer to generate an enzymatic product which incorporates a binding species and a detectable species covalently linked.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 9, line 56 to column 10, line 7:

In addition to the detection formats and assay formats described above which are based on the use of a solid phase to enable the analysis of formed complexes. Methods also exist for the detection of formed complexes which make use of the enhanced proximity of labels and binding species caused by the action of the template depended nucleic acid synthase enzymes of the present invention. Methods which make use of proximity to allow detection and quantitation are fluorescent energy transfer, scintillation proximity assay systems (Amersham, Dover, Del.), enzyme channeling assay systems (Litman et al (1980) Anal [Chem] *Biochem*, 106, 223), luminescent oxygen channeling assay systems (Ullman et al Clin Chem (1996) 42, 1518). These detection methods are also contemplated for the detection of nucleic acid using the methods of the invention to incorporate labels or binding species which are able to generate signals dependent on proximity of the incorporated groups into the products of the template dependent nucleic acid synthase enzymes.

AS A RESULT OF REEXAMINATION, IT HAS BEEN DETERMINED THAT:

Claims 1–49 are determined to be patentable as amended.

Claims 50–62, dependent on an amended claim, are determined to be patentable.

New claims 63–97 are added and determined to be patentable.

1. A method for determining total nucleic acid in a sample, which comprises:
   a) mixing at least one random primer at least 4 nucleotides in length, having at least one detectable species with [a] *said* sample which may contain nucleic acid,
   b) adding at least one *first* nucleotide triphosphate having at least one binding species and optionally at least one second nucleotide triphosphate,
   c) adding at least one nucleic acid polymerase,
   d) incubating the mixture of step c), under conditions which allow said at least one nucleic acid polymerase to be active,
   e) contacting the mixture of step d) with at least one solid phase,
   f) measuring total nucleic acid in said sample by measuring the total amount of said at least one detectable species bound to said solid phase, and
   g) determining whether the total nucleic acid in said sample is higher or lower than a threshold amount of contamination, wherein the threshold amount of contamination is equal to or less than 100 pg *per dose*.

2. A method for determining total nucleic acid in a sample, which comprises:
   a) mixing at least one random primer at least 4 nucleotides in length, having at least one binding species with [a] *said* sample which may contain nucleic acid,
   b) adding at least one *first* nucleotide triphosphate having at least one detectable species and optionally at least one second nucleotide triphosphate,
   c) adding at least one nucleic acid polymerase,
   d) incubating the mixture of step c), under conditions which allow said at least one nucleic acid polymerase to be active,
   e) contacting the mixture of step d) with at least one solid phase,
   f) measuring total nucleic acid in said sample by measuring the total amount of said at least one detectable species bound to said solid phase, and
   g) determining whether the total nucleic acid in said sample is higher or lower than a threshold amount of contamination, wherein the threshold amount of contamination is equal to or less than 100 pg *per dose*.

3. A method for determining total nucleic acid in a sample, which comprises:
   a) mixing at least one random primer at least 4 nucleotides in length with [a] *said* sample which may contain nucleic acid,
   b) adding at least one *first* nucleotide triphosphate having at least one binding species and optionally at least one *second* nucleotide triphosphate having at least one detectable species and optionally at least one [second] *third* nucleotide triphosphate,
   c) adding at least one nucleic acid polyermase,
   d) incubating the mixture of step c), under conditions which allow said at least one nucleic acid polymerase to be active,
   e) contacting the mixture of step d) with at least one solid phase,
   f) measuring total nucleic acid in said sample by measuring the total amount of said at least one detectable species or the amount of said at least one binding species bound to said solid phase, and
   g) determining whether the total nucleic acid in said sample is higher or lower than a threshold amount of contamination, wherein the threshold amount of contamination is equal to or less than 100 pg *per dose*.

4. A method for determining total nucleic acid in a sample, which comprises:
   a) mixing at least one first labeled random primer at least 4 nucleotides in length having at least one binding species and at least one second random primer at least 4 nucleotides in length having at least one detectable species, with [a] *said* sample which may contain nucleic acid,
   b) adding at least one nucleic acid ligase,
   c) incubating the mixture of step b), under conditions which allow said at least one nucleic acid ligase to be active,
   d) contacting the mixture of step c) with at least one solid phase,
   e) measuring total nucleic acid in said sample by measuring the total amount of said at least one detectable species or the amount of said at least one binding species bound to said solid phase, and f) determining whether the total nucleic acid in said sample is higher or lower than a threshold amount of contamination, wherein the threshold amount of contamination is equal to or less than 100 pg *per dose*.

5. A method for determining total nucleic acid in a sample, which comprises:
 a) mixing at least one first labeled random primer at least 4 nucleotides in length having at least one binding species and at least one second random primer at least 4 nucleotides in length having at least one detectable species, with [a] *said* sample which may contain nucleic acid,
 b) adding at least one nucleic acid ligase and at least one nucleic acid polymerase,
 c) incubating the mixture of step b), under conditions which allow said at least one nucleic acid ligase and at least one nucleic acid polymerase to be active,
 d) contacting the mixture of step c) with at least one solid phase,
 e) measuring total nucleic acid in said sample by measuring the total amount of said at least one detectable species or the amount of said at least one binding species bound to said solid phase, and
 f) determining whether the total nucleic acid in said sample is higher or lower than a threshold amount of contamination, wherein the threshold amount of contamination is equal to or less than 100 pg *per dose*.

6. [A] *The* method as in claim 1, wherein said at least one binding species is selected from the group consisting of biotin, avidin, streptavidin, antibody, antigen, lectin, receptor, ligand, hormone, nucleic acid sequence, mimitope and nucleic acid base pairing polymer.

7. [A] *The* method as in claim 1, wherein said at least one detectable species is selected from the group consisting of biotin, avidin, streptavidin, antibody, antigen, lectin, receptor, ligand, hormone, nucleic acid sequence, mimitope, nucleic acid base pairing polymer, flourescent molecule, electrochemiluminescent molecule, radioactive molecule, colored molecule, peroxidase, alkaline phosphatase and enzymes capable of producing a detectable species.

8. [A] *The* method as in claim 1, wherein said at least one nucleic acid polymerase is selected from the group consisting of Taq DNA polymerase, T4 DNA polymerase, [Klenow fragment,] Pfu DNA polymerase, Exo-Pfu DNA polymerase, E. coli DNA polymerase I, Klenow fragment of DNA polymerase I, MMLV reverse transcriptase and AMV reverse transcriptase.

9. [A] *The* method as in claim 1, wherein said at least one solid phase is selected from the group consisting of fiber, fibril, plastic surface, plastic bead, magnetic bead, plastic tube, gold surface, metal surface, metal bead and colloids.

10. [A] *The* method as in claim 1, wherein said at least one *first* nucleotide triphosphate is selected from the group consisting of dATP, dGTP, dCTP, dUTP, dTTP, ATP, CTP, GTP, TTP, UTP inosine TP, propyne dCTP, propyne dUTP, 5-bromo dCTP, 5-iodo dUTP, 5-fluoro dUTP, -6 methyl dGTP, 7-deaza dGTP, N-6 methyl-2'-dATP, biotin-dATP, biotin-dCTP, biotin-dUTP, digoxigenin dUTP, digoxigenin UTP and biotin ddUTP.

11. [A] *The* method as in claim 1, wherein said at least one random primer is 4–70 nucleotides *in length*.

12. [A] *The* method as in claim 1, wherein said conditions comprise a solution with a pH between 5.5 and 9.5, a nucleotide triphosphate concentration between 1 pM and 10 mM, a [Mg2 +] $Mg^{2+}$ concentration between 0.05 mM and 500 mM, and a reducing agent concentration between 0 and 500 mM, wherein the sum of the molarities is between 1 mM and 500 mM.

13. [A] *The* method as in claim 4, wherein said at least one ligase is selected from the group consisting of Pfu DNA ligase, T4 DNA ligase, Taq DNA ligase, T4 RNA ligase, and E. coli DNA ligase.

14. [A] *The* method as in claim 1, wherein said random primer is from 4 to 20 nucleotides in length.

15. [A] *The* method as in claim 14, wherein said at least one detectable species is selected from the group consisting of biotin, nucleic acid sequence, nucleic acid base pairing linear polymer, fluorescent molecule, electrochemiluminescent molecule, radioactive molecule, peroxidase and alkaline phosphatase.

16. [A] *The* method as in claim 14, wherein said at least one binding species is selected from the group consisting of biotin, antigen, lectin, ligand, hormone, nucleic acid sequence, mimitope and nucleic acid base pairing linear polymer.

17. [A] *The* method as in claim 14, wherein said at least one nucleic acid polymerase is selected from the group consisting of Taq DNA polymerase, [Klenow fragment (3'–5') of] E. coli DNA polymerase I and Klenow fragment DNA polymerase I.

18. [A] *The* method as in claim 14, wherein said at least one solid phase is selected from the group consisting of magnetic bead, plastic plate and polymer bead.

19. [A] *The* method as in claim 14, wherein said at least one *first* nucleotide triphosphate is selected from the group consisting of dATP, dGTP, dCTP, dUTP, dTTP, 7-deaza dGTP, biotin-dATP, biotin-dCTP, biotin-dUTP, digoxigenin dUTP, digoxigenin UTP and biotin ddUTP.

20. [A] *The* method as in claim 14, wherein said random primer is 6–10 nucleotides in length.

21. [A] *The* method as in claim 14, wherein said conditions comprise those optimal for Klenow fragment of DNA polymerase I to synthesize DNA.

22. [A] *The* method as in claim 20, wherein said [NTP] *at least one first nucleotide triphosphate* is a dNTP.

23. A method for determining total nucleic acid in a sample, which comprises:
 a) mixing at least one random primer at least 4 nucleotides in length having at least one detectable species, with [a] *said* sample which may contain nucleic acid,
 b) adding at least one *first* nucleotide triphosphate having at least one binding species and optionally at least one second nucleotide triphosphate,
 c) adding at least one nucleic acid polymerase,
 d) incubating the mixture of step c), under conditions which allow said at least one nucleic acid polymerase to be active,
 e) measuring total nucleic acid in said sample by measuring the total amount of said at least one detectable species or the amount of said at least one binding species, and
 f) determining whether the total nucleic acid in said sample is higher or lower than a threshold amount of contamination, wherein the threshold amount of contamination is equal to or less than 100 pg *per dose*.

24. A method for determining total nucleic acid in a sample, which comprises:
 a) mixing at least one random primer at least 4 nucleotides in length, having at least one binding species, with [a] *said* sample which may contain nucleic acid,
 b) adding at least one *first* nucleotide triphosphate having at least one detectable species and optionally at least one second nucleotide triphosphate,
 c) adding at least one nucleic acid polymerase, d) incubating the mixture of step c), under conditions which allow said at least one nucleic acid polymerase to be active, e) measuring total nucleic acid in said sample by measuring the total amount of said at least one detectable species or the amount of said at least one binding species, and f) determining whether the total nucleic acid in said sample is higher or lower than a threshold amount of contamination, wherein the threshold amount of contamination is equal to or less than 100 pg *per dose*.

25. A method for determining total nucleic acid in a sample, which comprises:

a) mixing at least one random primer at least 4 nucleotides in length with [a] *said* sample which may contain nucleic acid, b) adding at least one *first* nucleotide triphosphate having at least one binding moiety and optionally at least one second nucleotide triphosphate having at least one label and optionally at least one *third* nucleotide triphosphate, c) adding at least one nucleic acid polymerase, d) incubating the mixture of step c), under conditions which allow said at least one nucleic acid polymerase to be active, e) measuring total nucleic acid in said sample by measuring the total amount of said at least one label or the amount of said at least one binding moiety, and f) determining whether the total nucleic acid in said sample is higher or lower than a threshold amount of contamination, wherein the threshold amount of contamination is equal to or less than 10 pg *per dose*.

26. A method for determining total nucleic acid in a sample, which comprises:

a) mixing at least one *first* labeled random primer at least 4 nucleotides in length having at least one binding species and optionally at least one second random primer at least 4 nucleotides in length having at least one detectable species, with [a] *said* sample nucleic acid, b) adding at least one nucleic acid ligase, c) incubating the mixture of step b), under conditions which allow said at least one nucleic acid ligase to be active, d) measuring total nucleic acid in said sample by measuring the total amount of said at least one detectable species or the amount of said at least one binding species, and e) determining whether the total nucleic acid in said sample is higher or lower than a threshold amount of contamination, wherein the threshold amount of contamination is equal to or less than 100 pg *per dose*.

27. A method for determining total nucleic acid in a sample, which comprises:

a) mixing at least one *first* labeled random primer at least 4 nucleotides in length having at least one binding species and optionally at least one second random primer at least 4 nucleotides in length having at least one detectable species, with [a] *said* sample which may contain nucleic acid, b) adding at least one nucleic acid ligase and at least one nucleic acid polymerase, c) adding at least one nucleotide triphosphate, d) incubating the mixture of step c), under conditions which allow said at least one nucleic acid ligase and at least one nucleic acid polymerase to be active, e) measuring total nucleic acid in said sample by measuring the total amount of said at least one detectable species or the amount of said at least one binding species, and f) determining whether the total nucleic acid in said sample is higher or lower than a threshold amount of contamination, wherein the threshold amount of contamination is equal to or less than 100 pg *per dose*.

28. [A] *The* method as in claim 23, wherein said at least one detectable species is selected from the group consisting of biotin, avidin, streptavidin, antibody, antigen, lectin, receptor, ligand, hormone, nucleic acid sequence, mimitope, nucleic acid base pairing linear polymer, fluorescent molecule, electrochemiluminescent molecule, radioactive molecule, colored molecule, peroxidase, alkaline phosphatase and enzymes capable of producing a detectable species.

29. [A] *The* method as in claim [1] *23*, wherein said at least one nucleic acid polymerase is selected from the group consisting of Taq DNA polymerase, T4 DNA polymerase, [Klenow fragment,] Pfu DNA polymerase, Exo-Pfu DNA polymerase, E. coli DNA polymerase I, Klenow fragment of DNA polymerase I, MMLV reverse transcriptase and AMV reverse transcriptase.

30. [A] *The* method as in claim 23, wherein said at least one *first* nucleotide triphosphate is selected from the group consisting of dATP, dGTP, dCTP, dUTP, dTTP, ATP, CTP, GTP, TTP, UTP inosine TP, propyne dCTP, propyne dUTP, 5-bromo dCTP, 5-iodo dUTP, 5- fluoro dUTP, O-6 methyl dGTP, 7-deaza dGTP, N-6 methyl-2'-dATP, biotin-dATP, biotin-dCTP biotin-dUTP, digoxigenin dUTP, digoxigenin UTP and biotin ddUTP.

31. [A] *The* method as in claim 23, wherein said at least one random primer is 4–70 nucleotides *in length*.

32. [A] *The* method as in claim 23, wherein said conditions comprise a solution with a pH between 5.5 and 9.5, a nucleotide triphosphate concentration between 1 pM and 10 mM, a [Mg2+] $Mg^{2+}$ concentration between 0.05 mM and 500 mM, and a reducing agent concentration between 0 and 500 mM, where the sum of the molarities is between 1 [M] *mM* and 500 mM.

33. [A] *The* method as in claim 26, wherein said at least one ligase is selected from the group consisting of Pfu DNA ligase, T4 DNA ligase, Taq DNA ligase, T4 RNA ligase and E. coli DNA ligase.

34. A method for determining total nucleic acid in a sample, which comprises:

a) mixing at least one random primer at least 4 nucleotides in length having at least one first label, with [a] *said* sample nucleic acid, b) adding at least one *first* nucleotide triphosphate having at least one second label and optionally at least one second nucleotide triphosphate, c) adding at least one nucleic acid polymerase, d) incubating the mixture of step c), under conditions which allow said at least one nucleic acid polymerase to be active, e) measuring total nucleic acid in said sample by measuring the total amount of said at least one first label or the amount of said at least one second label, and f) determining whether the total nucleic acid in said sample is higher or lower than a threshold amount of contamination, wherein the threshold amount of contamination is equal to or less than 100 pg *per dose*.

35. A method for determining total nucleic acid in a sample, which comprises:

a) mixing at least one *first* labeled random primer at least 4 nucleotides in length having at least one first label species and optionally at least one second random primer at least 4 nucleotides in length having at least one second label, with [a] *said* sample which may contain nucleic acid, b) adding at least one nucleic acid ligase, c) incubating the mixture of step b), under conditions which allow said at least one nucleic acid ligase to be active, d) measuring total nucleic acid in said sample by measuring the total amount of said at least one first label or the amount of said at least one second label, and e) determining whether the total nucleic acid in said sample is higher or lower than a threshold amount of contamination, wherein the threshold amount of contamination is equal to or less than 100 pg *per dose*.

36. A method for determining total nucleic acid in a sample, which comprises:

a) mixing at least one *first* labeled random primer at least 4 nucleotides in length having at least one first label and optionally at least one second random primer at least 4 nucleotides in length having at least one second label, with [a] *said* sample which may contain nucleic acid, b) adding at least one nucleic acid ligase and at least one nucleic acid polymerase, c) adding at least one nucleotide triphosphate, d) incubating the mixture of step c), under conditions which allow said at least one nucleic acid ligase and at least one nucleic acid polymerase to be active, e) measuring total nucleic acid in said sample by measuring the total amount of said at least one first label or the amount of said at least one second label, and f) determining whether the total nucleic acid in said sample is higher or lower than a threshold amount of contamination, wherein the threshold amount of contamination is equal to or less than 100 pg *per dose*.

37. The method of claim 1, wherein said method is capable of detecting total nucleic acid in amounts as low as 5 pg *per dose*.

38. The method of claim 2, wherein said method is capable of detecting total nucleic acid in amounts as low as 5 pg *per dose*.

39. The method of claim 3, wherein said method is capable of detecting total nucleic acid in amounts as low as 5 pg *per dose*.

40. The method of claim 4, wherein said method is capable of detecting total nucleic acid in amounts as low as 5 pg *per dose*.

41. The method of claim 5, wherein said method is capable of detecting total nucleic acid in amounts as low as 5 pg *per dose*.

42. The method of claim 23, wherein said method is capable of detecting total nucleic acid in amounts as low as 5 pg *per dose*.

43. The method of claim 24, wherein said method is capable of detecting total nucleic acid in amounts as low as 5 pg *per dose*.

44. The method of claim 25, wherein said method is capable of detecting total nucleic acid in amounts as low as 5 pg *per dose*.

45. The method of claim 26, wherein said method is capable of detecting total nucleic acid in amounts as low as 5 pg *per dose*.

46. The method of claim 27, wherein said method is capable of detecting total nucleic acid in amounts as low as 5 pg *per dose*.

47. The method of claim 34, wherein said method is capable of detecting total nucleic acid in amounts as low as 5 pg *per dose*.

48. The method of claim 35, wherein said method is capable of detecting total nucleic acid in amounts as low as 5 pg *per dose*.

49. The method of claim 36, wherein said method is capable of detecting total nucleic acid in amounts as low as 5 pg *per dose*.

63. *The method as in claim 23, wherein said random primer is from 4 to 20 nucleotides in length.*

64. *The method as in claim 63, wherein said at least one detectable species is selected from the group consisting of biotin, nucleic acid sequence, nucleic acid base pairing linear polymer, fluorescent molecule, electrochemiluminescent molecule, radioactive molecule, peroxidase and alkaline phosphatase.*

65. *The method as in claim 63, wherein said at least one nucleic acid polymerase is selected from the group consisting of Taq DNA polymerase, E. coli DNA polymerase I and Klenow fragment of DNA polymerase I.*

66. *The method as in claim 63, wherein said at least one first nucleotide triphosphate is selected from the group consisting of dATP, dGTP, dCTP, dUTP, dTTP, 7-deaza dGTP, biotin-dATP, biotin-dCTP, biotin-dUTP, digoxigenin dUTP, digoxigenin UTP and biotin ddUTP.*

67. *The method as in claim 63, wherein said random primer is 6–10 nucleotides in length.*

68. *The method as in claim 63, wherein said conditions comprise those optimal for Klenow fragment of DNA polymerase I to synthesize DNA.*

69. *The method as in claim 67, wherein said at least one first nucleotide triphosphate is a dNTP.*

70. *The method as in claim 2, wherein said at least one binding species is selected from the group consisting of biotin, avidin, streptavidin, antibody, antigen, lectin, receptor, ligand, hormone, nucleic acid sequence, mimitope and nucleic acid base pairing polymer.*

71. *The method as in claim 2, wherein said at least one detectable species is selected from the group consisting of biotin, avidin, streptavidin, antibody, antigen, lectin, receptor, ligand, hormone, nucleic acid sequence, mimitope, nucleic acid base pairing polymer, fluorescent molecule, electrochemiluminescent molecule, radioactive molecule, colored molecule, peroxidase, alkaline phosphatase and enzymes capable of producing a detectable species.*

72. *The method as in claim 2, wherein said at least one nucleic acid polymerase is selected from the group consisting of Taq DNA polymerase, T4 DNA polymerase, Pfu DNA polymerase, Exo-Pfu DNA polymerase, E. coli DNA polymerase I, Klenow fragment of DNA polymerase I, MMLV reverse transcriptase and AMV reverse transcriptase.*

73. *The method as in claim 2, wherein said at least one solid phase is selected from the group consisting of fiber, fibril, plastic surface, plastic bead, magnetic bead, plastic tube, gold surface, metal surface, metal bead and colloids.*

74. *The method as in claim 2, wherein said at least one first nucleotide triphosphate is selected from the group consisting of dATP, dGTP, dCTP, dUTP, dTTP, ATP, CTP, GTP, TTP, UTP inosineTP, propyne dCTP, propyne dUTP, 5-bromo dCTP, 5-iodo dUTP, 5-fluoro dUTP, 0–6 methyl dGTP, 7-deaza dGTP, N-6 methyl-2'-dATP, biotin-dATP, biotin-dCTP, biotin-dUPT, digoxigenin dUTP, digoxigenin UTP and biotin ddUTP.*

75. *The method as in claim 2, wherein said at least one random primer is 4–70 nucleotides in length.*

76. *The method as in claim 2, wherein said conditions comprise a solution with a pH between 5.5 and 9.5, a nucle-* otide triphosphate concentration between 1 pM and 10 mM, a $Mg^{2+}$ concentration between 0.05 mM and 500 mM, and a reducing agent concentration between 0 and 500 mM, wherein the sum of the molarities is between 1 mM and 500 mM.

77. The method as in claim 2, wherein said random primer is from 4 to 20 nucleotides in length.

78. The method as in claim 77, wherein said at least one detectable species is selected from the group consisting of biotin, nucleic acid sequence, nucleic acid base pairing linear polymer, fluorescent molecule, electrochemiluminescent molecule, radioactive molecule, peroxidase and alkaline phosphatase.

79. The method as in claim 77, wherein said at least one binding species is selected from the group consisting of biotin, antigen, lectin, ligand, hormone, nucleic acid sequence, mimitope and nucleic acid base pairing linear polymer.

80. The method as in claim 77, wherein said at least one nucleic acid polymerase is selected from the group consisting of Taq DNA polymerase, E. coli DNA polymerase I and Klenow fragment of DNA polymerase I.

81. The method as in claim 77, wherein said at least one solid phase is selected from the group consisting of magnetic bead, plastic plate and polymer bead.

82. The method as in claim 77, wherein said at least one first nucleotide triphosphate is selected from the group consisting of dATP, dGTP, dCTP, dUPT, dTTP, 7-deaza dGTP, biotin-dATP, biotin-dCTP, biotin-dUTP, digoxigenin dUTP, digoxigenin UTP and biotin ddUTP.

83. The method as in claim 77, wherein said random primer is 6–10 nucleotides in length.

84. The method as in claim 77, wherein said conditions comprise those optimal for Klenow fragment of DNA polymerase I to synthesize DNA.

85. The method as in claim 83, wherein said at least one first nucleotide triphosphate is a dNTP.

86. The method as in claim 24, wherein said at least one detectable species is selected from the group consisting of biotin, avidin, streptavidin, antibody, antigen, lectin, receptor, ligand, hormone, nucleic acid sequence, mimitope, nucleic acid base pairing linear polymer, fluorescent molecule, electrochemiluminescent molecule, radioactive molecule, colored molecule, peroxidase, alkaline phosphatase and enzymes capable of producing a detectable species.

87. The method as in claim 24, wherein said at least one nucleic acid polymerase is selected from the group consisting of Taq DNA polymerase, T4 DNA polymerase, Pfu DNA polymerase, Exo-Pfu DNA polymerase, E. coli DNA polymerase I, Klenow fragment of DNA polymerase I, MMLV reverse transcriptase and AMV reverse transcriptase.

88. The method as in claim 24, wherein said at least first one nucleotide triphosphate is selected from the group consisting of dATP, dGTP, dCTP, dUTP, dTTP, ATP, CTP, GTP, TTP, UTP inosineTP, propyne dCTP, propyne dUTP, 5-bromo dCTP, 5-iodo dUTP, 5-fluoro dUTP, 0–6 methyl dGTP, 7-deaza dGTP, N-6 methyl-2'-dATP, biotin-dATP, biotin-dCTP, biotin-dUTP, digoxigenin dUTP, digoxigenin UTP and biotin ddUTP.

89. The method as in claim 24, wherein said at least one random primer is 4–70 nucleotides in length.

90. The method as in claim 24, wherein said conditions comprise a solution with a pH between 5.5 and 9.5, a nucleotide triphosphate concentration between 1 pM and 10 mM, a $Mg^{2+}$ concentration between 0.05 mM and 500 mM, and a reducing agent concentration between 0 and 500 mM, where the sum of the molarities is between 1 mM and 500 mM.

91. The method as in claim 24, wherein said random primer is from 4 to 20 nucleotides in length.

92. The method as in claim 91, wherein said at least one detectable species is selected from the group consisting of biotin, nucleic acid sequence, nucleic acid base pairing linear polymer, fluorescent molecule, electrochemiluminescent molecule, radioactive molecule, peroxidase and alkaline phosphatase.

93. The method as in claim 91, wherein said at least one nucleic acid polymerase is selected from the group consisting of Taq DNA polymerase, E. coli DNA polymerase I and Klenow fragment of DNA polymerase I.

94. The method as in claim 91, wherein said at least one first nucleotide triphosphate is selected from the group consisting of dATP, dGTP, dCTP, dUTP, dTTP, 7-deaza dGTP, biotin-dATP, biotin-dCTP, biotin-dUTP, digoxigenin dUTP, digoxigenin UTP and biotin ddUTP.

95. The method as in claim 91, wherein said random primer is 6–10 nucleotides in length.

96. The method as in claim 91, wherein said conditions comprise those optimal for Klenow fragment of DNA polymerase I to synthesize DNA.

97. The method as in claim 95, wherein said at least one first nucleotide triphosphate is a dNTP.

* * * * *